United States Patent
Hilvo

(10) Patent No.: US 10,534,001 B2
(45) Date of Patent: Jan. 14, 2020

(54) METHODS FOR DETECTING OVARIAN CANCER

(71) Applicant: Zora Biosciences OY, Espoo (FI)

(72) Inventor: Mika Hilvo, Helsinki (FI)

(73) Assignee: ZORA BIOSCIENCES OY, Espoo (FI)

(*) Notice: Subject to any disclaimer, the term of this patent is extended or adjusted under 35 U.S.C. 154(b) by 176 days.

(21) Appl. No.: 15/513,755

(22) PCT Filed: Oct. 2, 2015

(86) PCT No.: PCT/FI2015/050654
§ 371 (c)(1),
(2) Date: Mar. 23, 2017

(87) PCT Pub. No.: WO2016/051020
PCT Pub. Date: Apr. 7, 2016

(65) Prior Publication Data
US 2017/0285036 A1    Oct. 5, 2017

(30) Foreign Application Priority Data
Oct. 2, 2014 (FI) .................................. 20145855

(51) Int. Cl.
| G01N 33/574 | (2006.01) |
| C07K 14/47 | (2006.01) |
| C12N 9/10 | (2006.01) |
| C12Q 1/6886 | (2018.01) |
| G01N 33/64 | (2006.01) |
| G01N 33/92 | (2006.01) |

(52) U.S. Cl.
CPC ... *G01N 33/57449* (2013.01); *C07K 14/4702* (2013.01); *C12N 9/10* (2013.01); *C12Q 1/6886* (2013.01); *G01N 33/64* (2013.01); *C12Q 2600/112* (2013.01); *C12Q 2600/118* (2013.01); *G01N 2800/7028* (2013.01)

(58) Field of Classification Search
CPC .... C07K 14/4702; C12N 9/10; C12Q 1/6886; C12Q 2600/112; C12Q 2600/118; G01N 2405/08; G01N 2570/00; G01N 2800/50; G01N 2800/7028; G01N 33/57449; G01N 33/64; G01N 33/92
See application file for complete search history.

(56) References Cited

U.S. PATENT DOCUMENTS

| 5,994,141 A | 11/1999 | Xu et al. |
| 2005/0170441 A1 | 8/2005 | Odunsi et al. |

FOREIGN PATENT DOCUMENTS

| WO | 2009/052186 A1 | 4/2009 |
| WO | 2009/096903 A1 | 8/2009 |
| WO | 2009/151967 A1 | 12/2009 |

(Continued)

OTHER PUBLICATIONS

Extended European Search Report dated Jun. 21, 2018 for European Application No. 15846140.0, 20 pages.

(Continued)

*Primary Examiner* — Savitha M Rao
(74) *Attorney, Agent, or Firm* — MH2 Technology Law Group, LLP

(57) ABSTRACT

The present description is related to the field of ovarian cancer diagnostics. It introduces novel biomarkers that can be used to detect presence of ovarian cancer and to provide a prognosis of the disease.

36 Claims, 26 Drawing Sheets

(56) References Cited

FOREIGN PATENT DOCUMENTS

| WO | 2011/041892 A1 | 4/2011 |
|---|---|---|
| WO | 2012/038525 A1 | 3/2012 |
| WO | 2012/168561 A1 | 12/2012 |
| WO | 2013/016700 A1 | 1/2013 |

OTHER PUBLICATIONS

Jelonek et al., "Cancer biomarkers and mass spectrometry-based analyses of phospholipids in body fluids", Clinical Lipidology, Feb. 1, 2013, vol. 8, No. 1, pp. 137-150.

Odunsi et al., "Detection of epithelial ovarian cancer using 1H-NMR-based metabonomics", International Journal of Cancer, 2004, vol. 113, No. 5, pp. 782-788.

Garcia et al., "Diagnosis of early stage ovarian cancer by 1H NMR metabonomics of serum explored by use of a micro-flow NMR probe", Journal of Proteome Research, Apr. 1, 2011, vol. 10, No. 4, pp. 1765-1771.

International Search Report and Written Opinion dated Mar. 9, 2016 from International Application No. PCT/FI2015/050654, 17 pages.

Perroud et al., "Pathways analysis of kidney cancer using proteomics and metabolic profiling", Molecular Cancer, Nov. 24, 2006, vol. 5, No. 64, pp. 1-17.

Wu et al., "GC/MS-based metabolomic approach to validate the role of urinary sarcosine and target biomarkers for human prostate cancer by microwave-assisted derivatization", Analytical and Bioanalytical Chemistry, Aug. 2011, vol. 401, No. 2, pp. 635-646.

Veldman R. J. et al., "Altered sphingolipid metabolism in multidrug-resistant ovarian cancer cells is due to uncoupling of glycolipid biosynthesis in the Golgi apparatus", The FASEB Journal, May 8, 2002, vol. 16, No. 9, pp. 1111-1113.

Partial Supplementary European Search Report dated Apr. 10, 2018 for European Application No. 15846140.0, 15 pages.

Hilvo et al., "Accumulated Metabolites of Hydroxybutyric Acid Serve as Diagnostic and Prognostic Biomarkers of Ovarian High-Grade Serous Carcinomas", Cancer Research, Feb. 15, 2016, vol. 76, No. 4, pp. 796-804.

METHODS FOR DETECTING OVARIAN CANCER

CROSS-REFERENCE TO RELATED APPLICATIONS

This application is a U.S. National Stage application of PCT/FI2015/050654 filed 2 Oct. 2015, which claims priority to Finnish Application No. 20145855 filed 2 Oct. 2014, the entire disclosures of which are hereby incorporated by reference in their entirety.

FIELD OF THE INVENTION

The present description is related to the field of diagnostic and prognostic biomarkers for ovarian cancer. In particular, it provides a novel in vitro screening method for assessing whether a subject is at risk to develop or is suffering from ovarian cancer. In addition, the present biomarkers can be used in methods to evaluate survival prognosis, effectiveness of treatment and success rate of tumor removal of ovarian cancer. Present biomarkers can be used to determine concentration of said biomarkers in tumor by measuring their concentration in blood serum or plasma.

BACKGROUND

Ovarian cancer is a heterogeneous disease of low prevalence but poor survival. According to the World Health Organization (WHO) statistics in 2012, worldwide there were estimated to be 239 000 new ovarian cancer cases, representing 4% of all cancers in women. According to the statistics 152 000 deaths were caused by ovarian cancer in 2012. Ovarian cancer is the eighth most frequent cause of cancer death among women, and major proportion of new ovarian cancers occur in countries with high or very high levels of human development. The incidence rates are highest in Northern and Eastern Europe, North America and Oceania, and tend to be relatively low in Africa and much of Asia. However, during the 1990s and 2000s the incidence rate e.g. in China increased dramatically. (World Health Organization World Cancer Report 2014). The most common ovarian cancers are ovarian carcinomas, which include five main subtypes, and of those the high-grade serous carcinoma is the most common one (accounts approximately 70% of the cases). Early diagnosis is critical for the survival of the patient, as e.g. for the stage I patients the 5-year survival rate is around 90%, whereas for the stage IV patients it is only around 20%. However, the diagnosis of ovarian cancer is difficult, and the disease tends to cause symptoms for the patients only when advanced to later stages, and, in addition, the symptoms mimic often those of other diseases. Therefore new diagnostic tools that could detect ovarian cancer already in the early stages would be essential for successful treatment of ovarian cancer patients.

Previous methods to detect ovarian cancer have relied on protein biomarker analyses and imaging methods. The main diagnostic methods for ovarian cancer at the moment include pelvic examination, CA-125 blood test and transvaginal ultrasound. CA-125 and HE4 are the only two biomarkers US FDA approved for monitoring disease recurrence or progression, but not for screening. The multivariate index assay, OVA1, consisting of several protein biomarkers has been FDA approved for triage of pelvic masses since 2009. (Nguyen et al., Women's Health, 2013, 9(2), 171-187). CA-125 has been reported to be a prognostic factor for overall and progression free survival in ovarian cancer, but also studies showing contradictory results exist. CA-125 levels are raised in approximately 90% of patients with advanced epithelial ovarian cancer, but only in 50% of patients with stage I disease (Gupta & Lis, Journal of Ovarian Cancer, 2009, 2:13). Thus, the golden standard, CA-125 is relatively good in detecting patients with advanced disease, but it is lacking sensitivity in other patients and its role in predicting survival is somewhat controversial.

Small molecules, including metabolites and lipids are attempting diagnostic tools as compared to protein biomarkers, since they directly reflect the changes in metabolism, which are known to occur already early in the tumor initiation and progression. Small changes in the gene expression or protein levels of specific pathways may result in large changes in the small molecule metabolite and lipid concentrations, as their levels can be considered to be an amplified output of the activity of the biological pathways. Despite some attempts to find small molecule markers for ovarian cancer, previous disclosures have failed to provide simple and reliable small molecule ovarian cancer biomarkers from blood serum that would have been taken into clinical practice. WO2009151967 describes a large panel of metabolic biomarker candidates and machine learning classification algorithms for ovarian cancer diagnostics. WO2012038525A1 describes a large panel of phospholipids as biomarkers for various cancers. WO2013016700 describes the use of classification algorithms to produce predictive models for epithelial ovarian cancer using data from mass spectrometry (MS) or nuclear magnetic resonance (NMR). NMR technique has been applied also in other disclosures describing potential biomarker candidates for ovarian cancer, such as WO2011041892 and US2005170441. However, the limitation of the previous investigations is in general the description of large panel of biomarkers, which could have not been narrowed down using other information from the cancer patients, such as prognosis or investigations on correlation of the biomarker levels between serum and tumor tissue. Furthermore, there are no disclosures showing how the information of single metabolites or metabolite combinations together with protein markers could be combined in order to give more accurate diagnostic and prognostic methods for ovarian cancer patients. Thus, focused small molecule biomarker panels would be extremely useful for better ovarian cancer diagnostics.

Definitions 3,4-DHBA—3,4-dihydroxybutyric acid
3-HBA—3-hydroxybutyric acid
AUC—area under the curve
CA-125—cancer antigen 125, carcinoma antigen 125, carbohydrate antigen 125
GC—gas chromatography
GCxGC—two dimensional gas chromatography
HE4—human epididymic protein 4
LC—liquid chromatography
lysoPC—lysophosphatidylcholine
MS—mass spectrometry
NMR—nuclear magnetic resonance
PC—phosphatidylcholine
PE—phosphatidylethanolamine
ROC—receiver operating characteristic
SM—sphingomyelin
TAG—triacylglycerol
TOF—time-of-flight
WHO—World Health Organization

DESCRIPTION OF THE INVENTION

Figure 1:
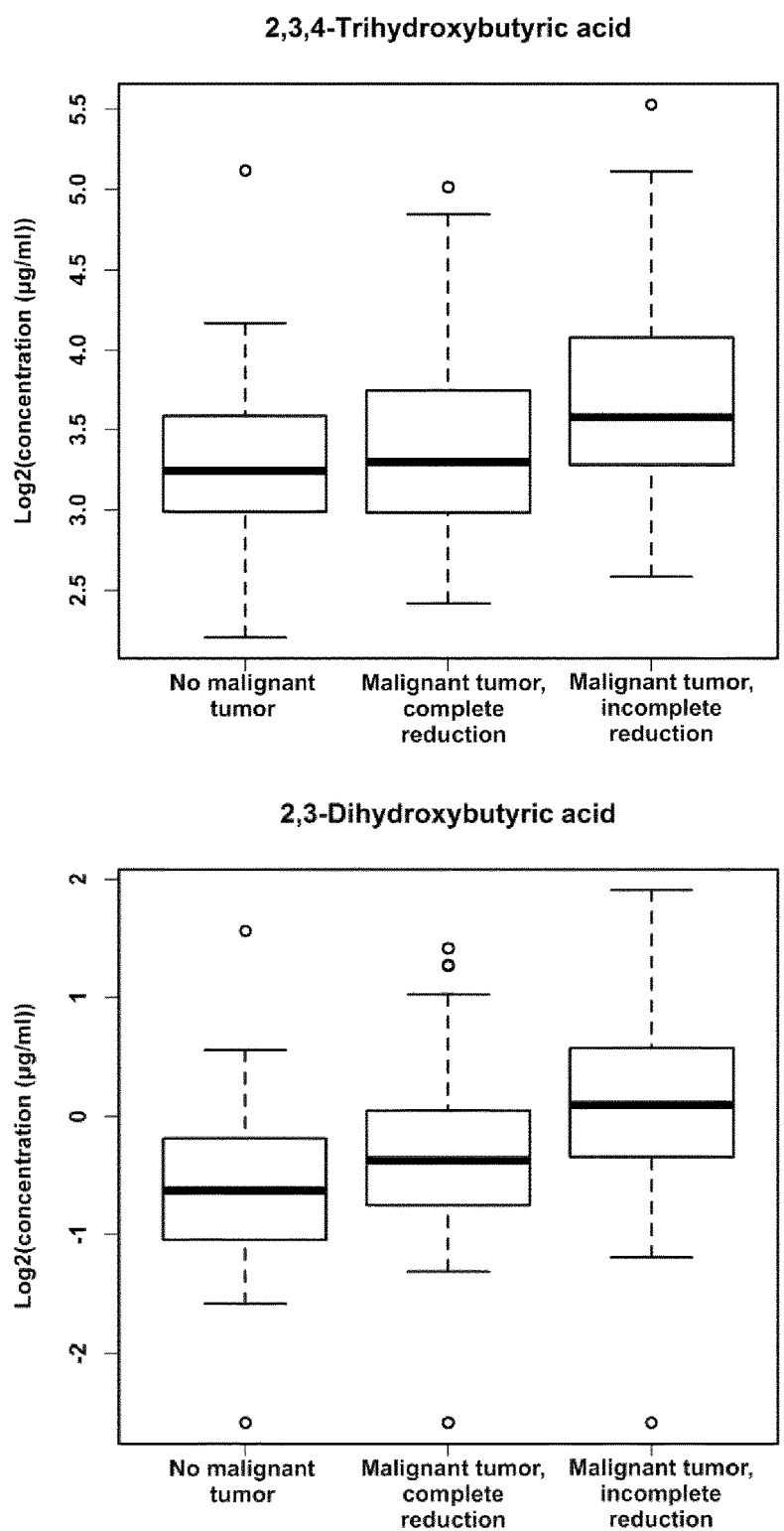
FIG. 1 discloses the concentration of the presently identified small molecule biomarkers and CA-125 in the serum of control group (no malignant tumor) as well as in ovarian cancer patients with or without complete tumor reduction during the surgery. In general, the small molecule biomarkers show a progressive trend in that the concentration is lowest in the control group and highest in the patients for which the tumor removal during the surgery has not been complete. This trend applies especially to di- and trihydroxybutyric acids. Sphingomyelins (SMs) show an opposite trend, where the concentration is highest in the subjects without malignant tumor and lowest in ovarian cancer patients without complete tumor reduction. CA-125 and 3-hydroxybutyric acid show a clear difference between controls and patients with malignant tumors, but in both cases there is no significant difference in the patients with and without tumor reduction, which indirectly implies that these molecules do not show a clear association to the amount of tumor mass present in the patient. The t-test values and log 2 fold changes for each of these molecules in the malignant vs. control as well as complete vs. incomplete tumor reduction comparisons are shown in Table 2.
Figure 1:
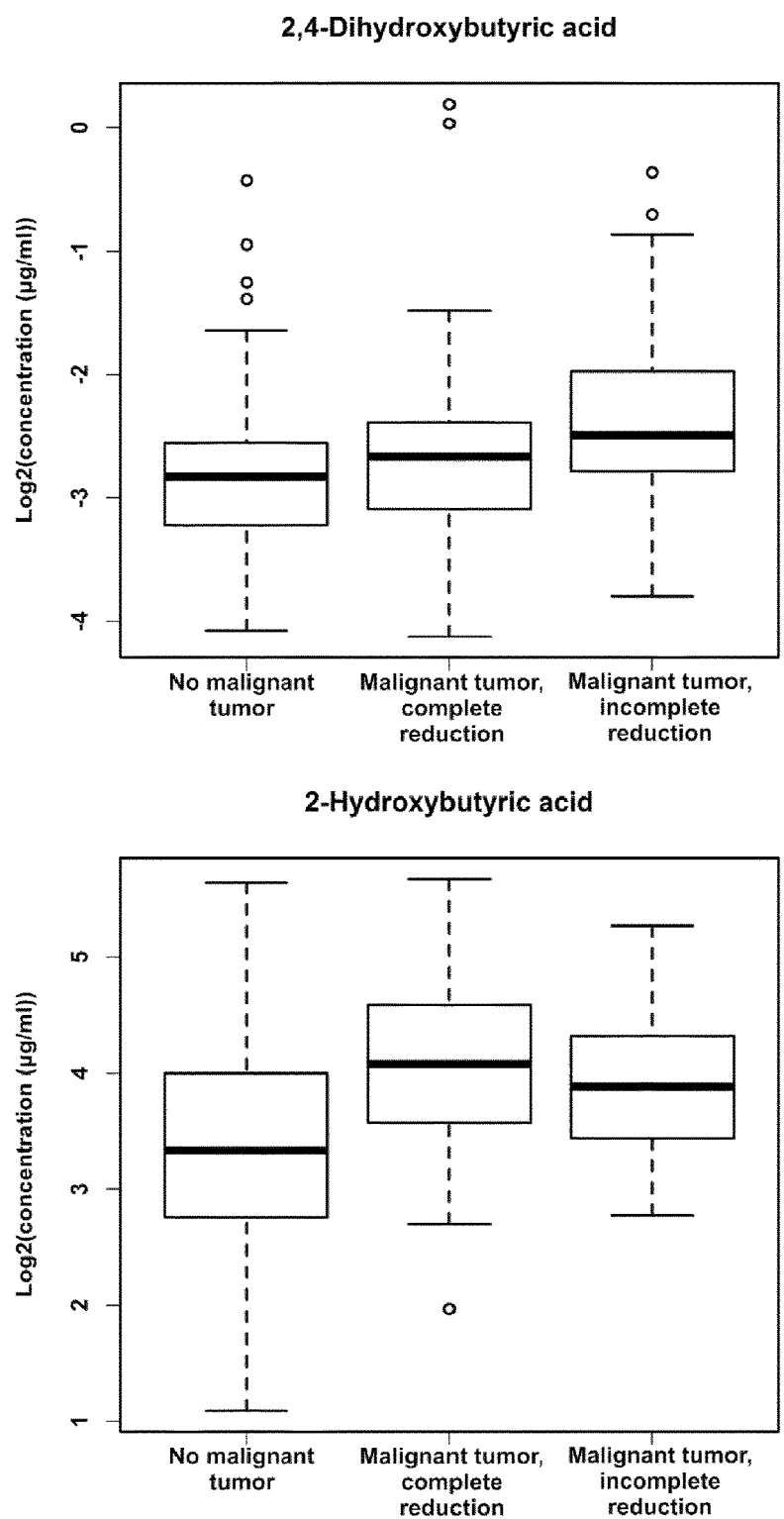
Figure 1:
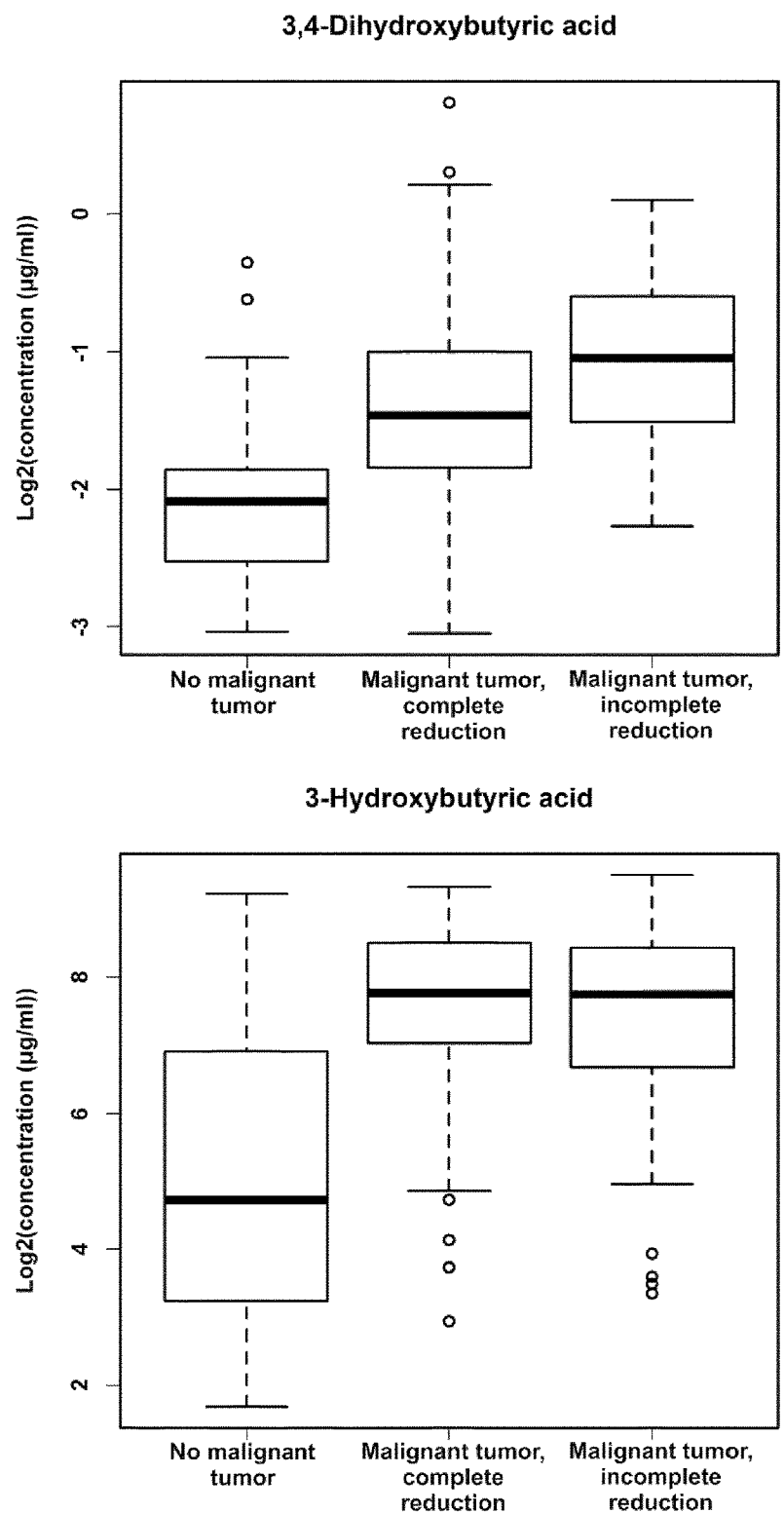
Figure 1:
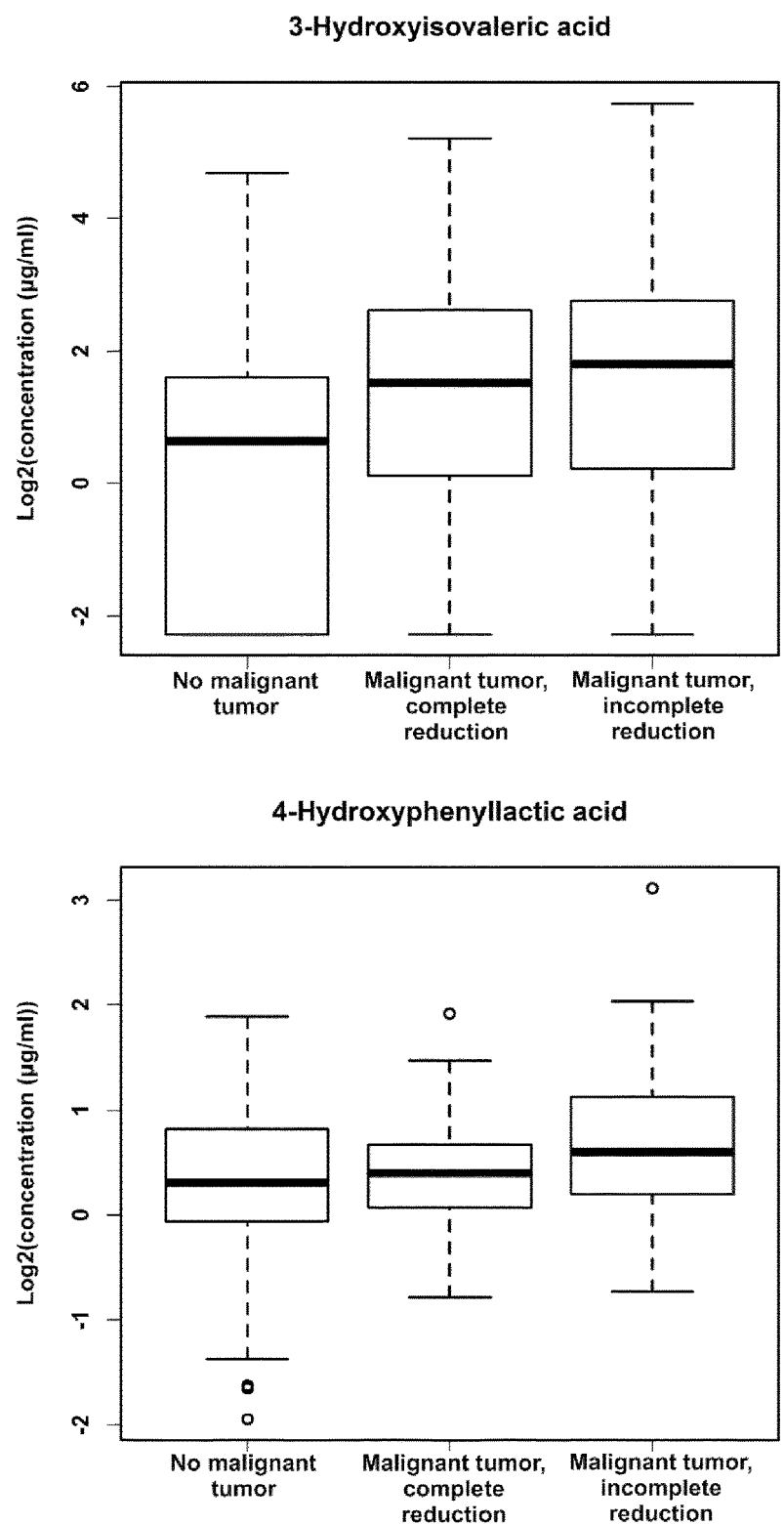
Figure 1:
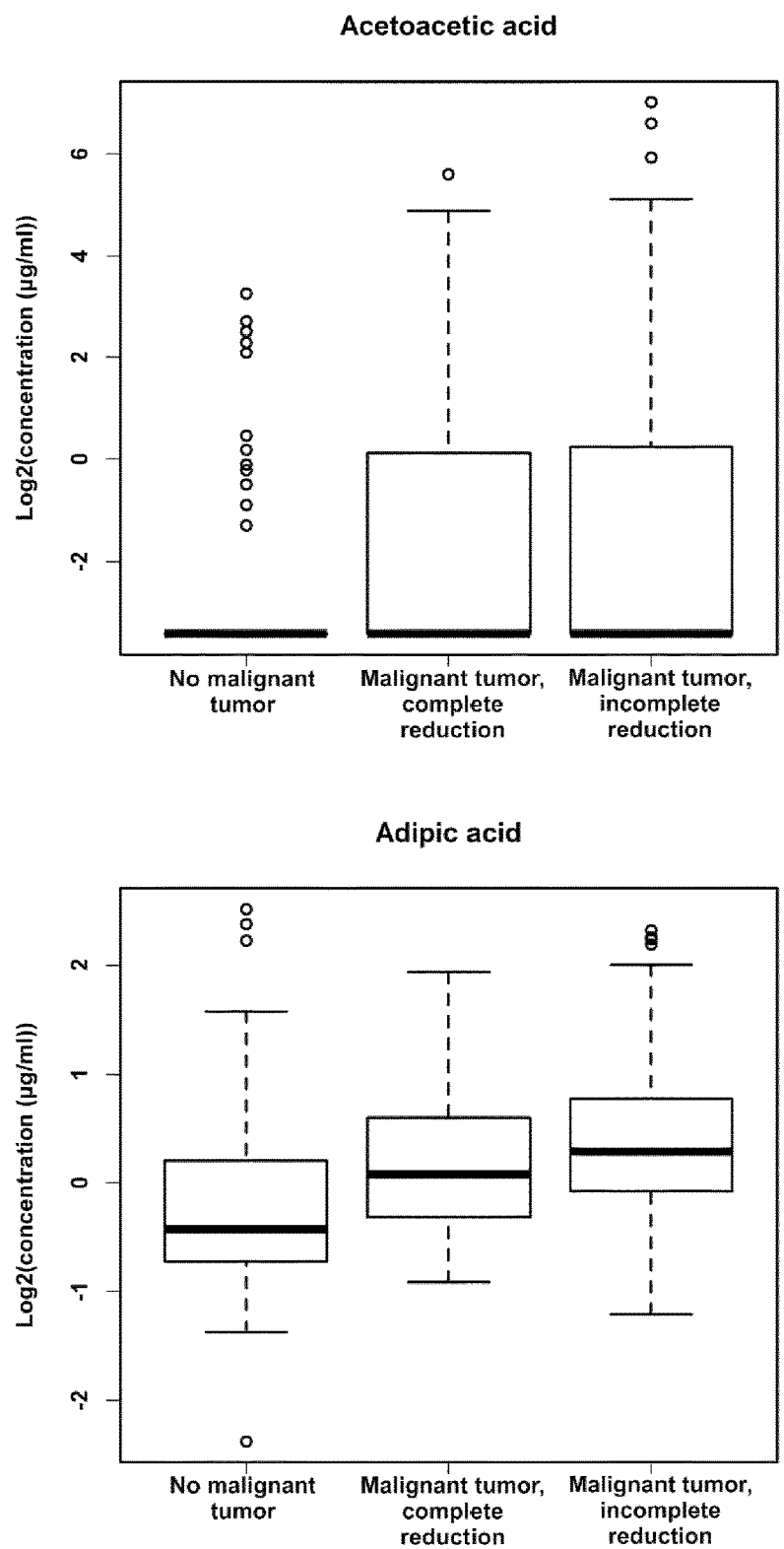
Figure 1:
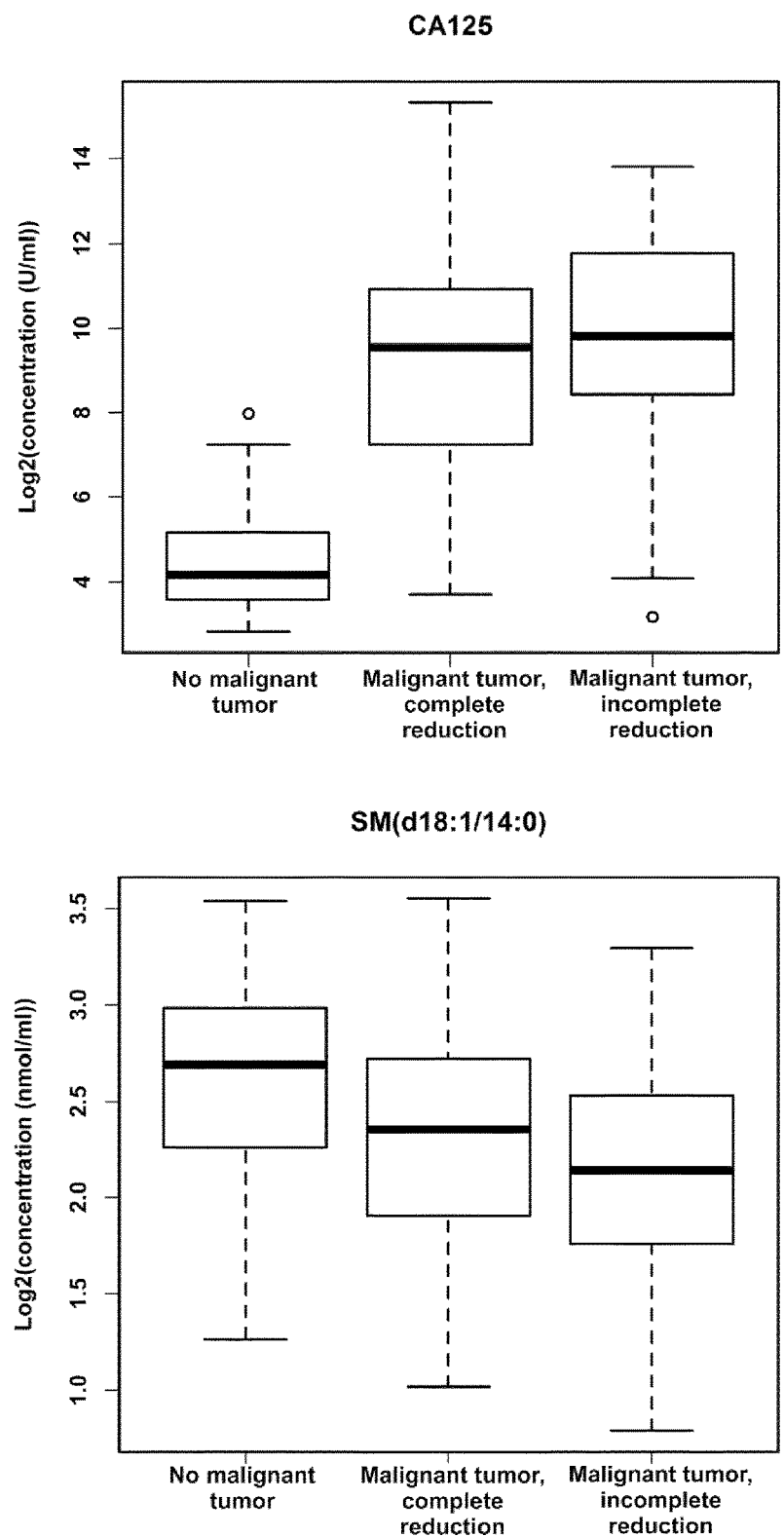
Figure 1:
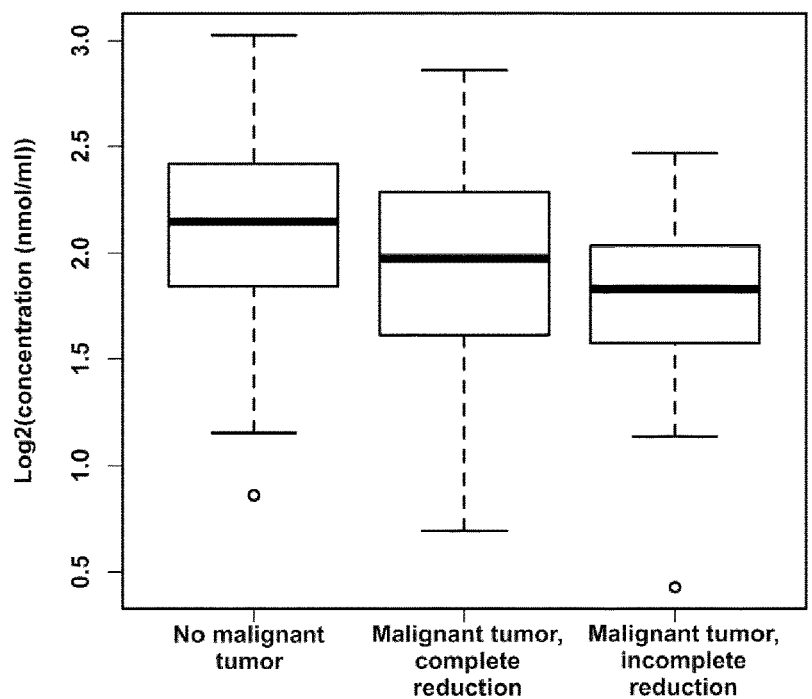
Figure 1:
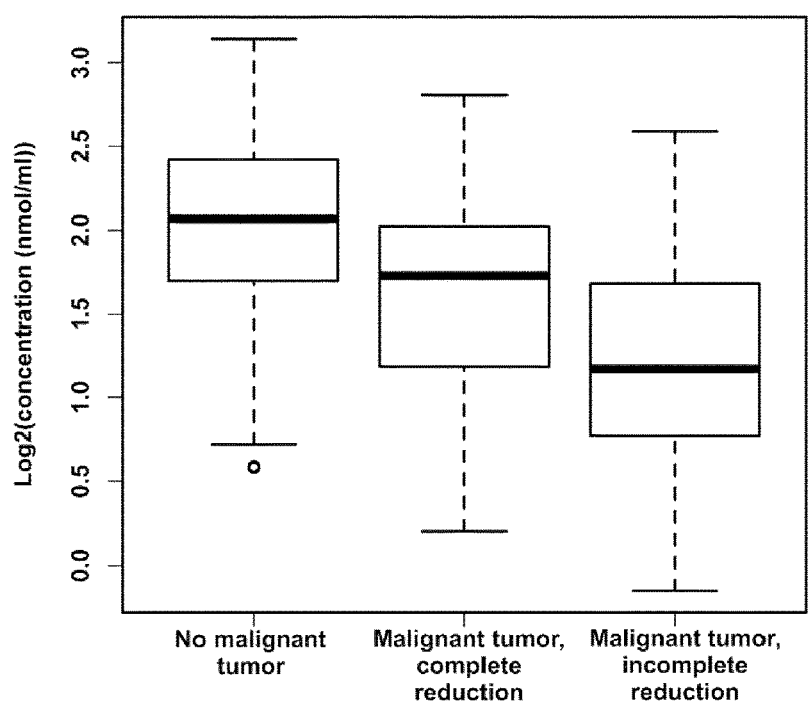
Figure 1:
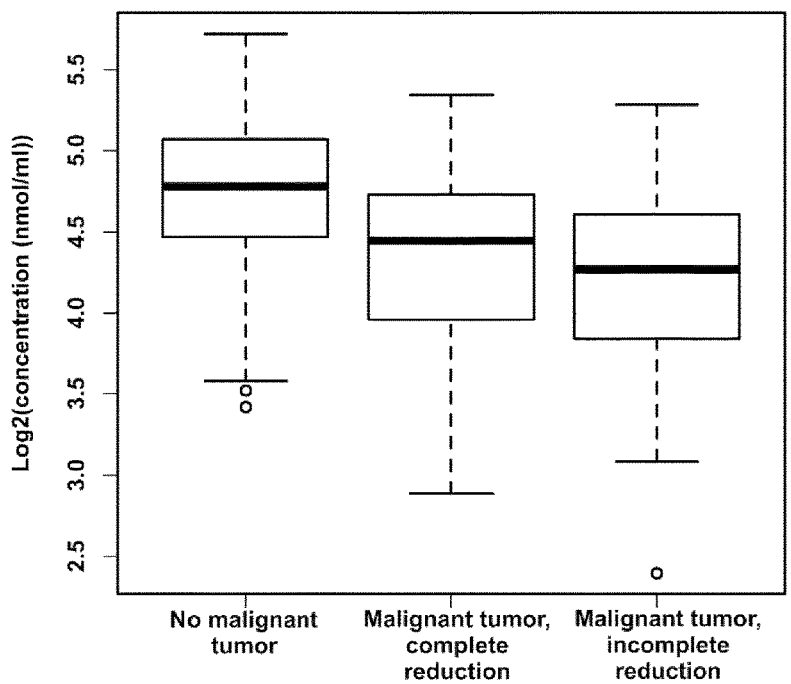
Figure 1:
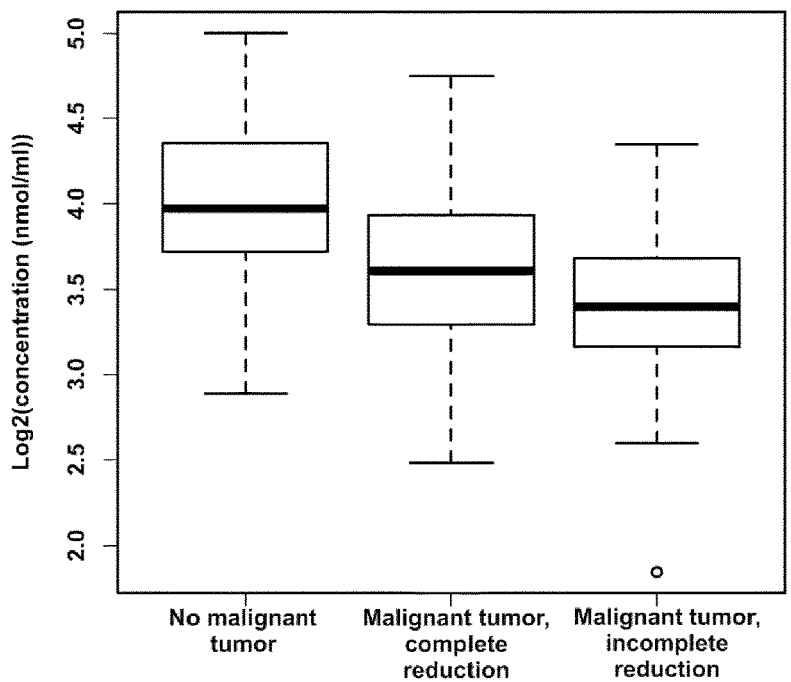
Figure 1:
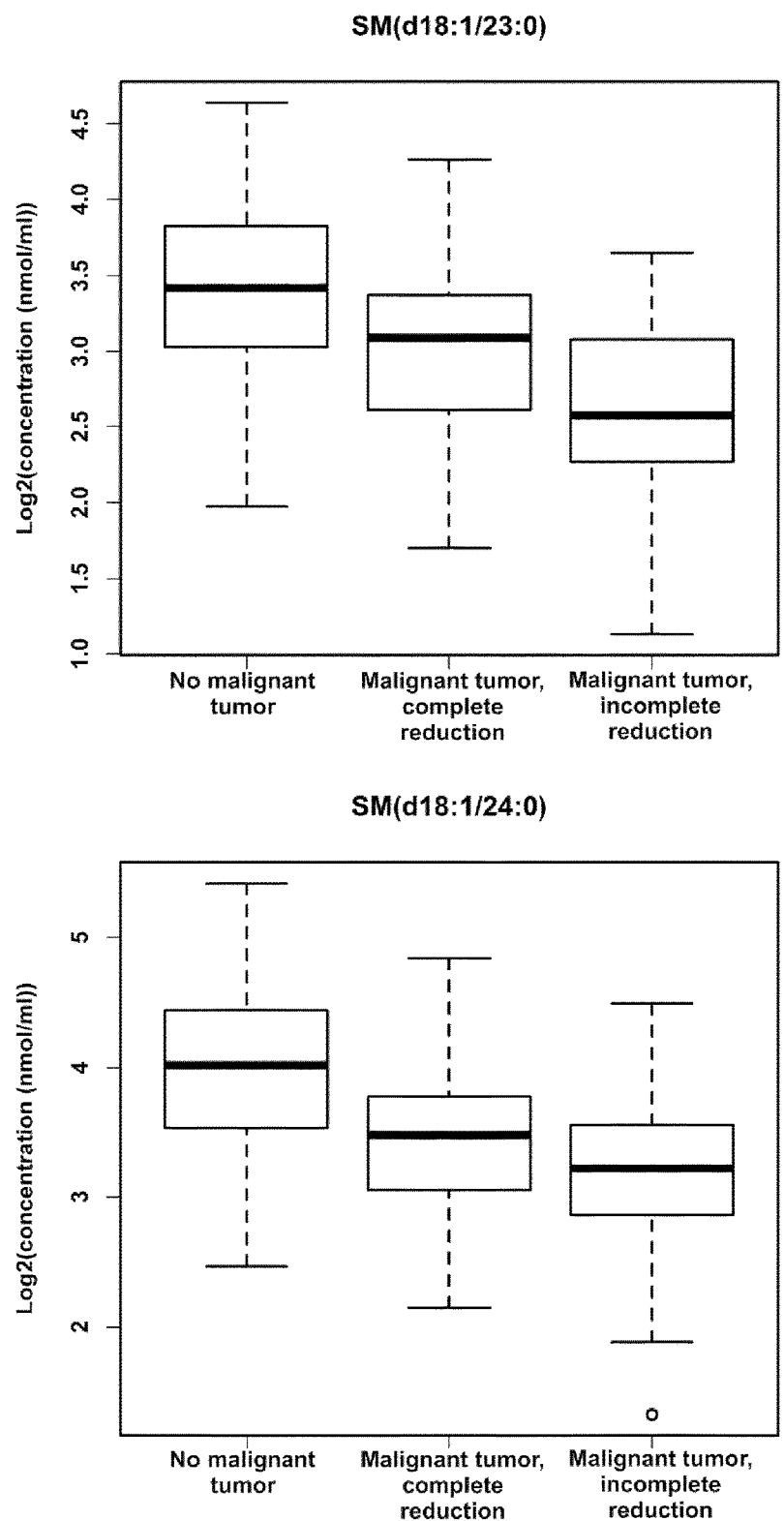

The present invention identifies small molecule ovarian cancer biomarkers by quantifying defined molecular species and combinations thereof. Importantly, the present invention shows value already at a level of single species concentrations. The present invention also provides for the first time a set of biomarkers that can be used, either alone or in combination, to determine their concentration in the ovarian cancer tumor by measuring the concentration in blood or even in breath, thereby simplifying the measurement.

The present inventor has surprisingly found novel small molecule biomarkers for ovarian cancer. Specifically, it has been found that each marker displays a characteristic increase or decrease in concentration in samples derived from subjects having ovarian cancer, and they are useful for the methods and uses in accordance with the present invention. The present biomarkers are sensitive and specific and they can be used in diagnostic and prognostic assays. They are particularly useful for early stage ovarian cancer, such as ovarian cancer in stage I or II. In addition for ovarian cancer diagnosis most of the present biomarkers also associate with survival of the patients, and therefore they have a dual role in both predicting the patients with malignant ovarian tumors as well as predicting also the prognosis for these patients. The present invention therefore represents a significant advantage over the prior methods currently used to diagnose and/or predict ovarian cancer.

Thus, the present small molecule biomarkers for ovarian cancer allow better diagnosis of or assessment of the risk to develop ovarian cancer. Further, the present markers find use in determining effectiveness of treatment and removal of tumors in patients having ovarian cancer.

Even though only a single small molecule biomarker can be used according to the present invention and it is sufficient to provide reliable results, it is preferred to use several biomarkers for increased reliability of the assessment. Further, the predictive or prognostic information from the small molecule biomarkers can be combined with protein biomarkers for ovarian cancer, such as CA-125, for early or late stage assessment.

According to the first aspect of the invention there is provided an in vitro screening method for assessing whether a subject is at risk to develop or is suffering from ovarian cancer comprising
  determining from a sample from said subject the concentration of at least one small molecule biomarker, wherein an increase or decrease in concentration of said sample, when compared to a control sample, is indicative of said subject suffering from or having an increased risk of developing ovarian cancer;
  (1) wherein the at least one small molecule biomarker whose increase in concentration is compared to the control is selected from the group consisting of dihydroxybutyric acids and trihydroxybutyric acid; and/or
  (2) wherein the at least one small molecule biomarker whose decrease in concentration is compared to the control is selected from the group consisting of sphingomyelins; and/or
  (3) wherein the at least one small molecule biomarker whose increase in concentration is compared to the control is a long chain triglyceride having acyl side chains comprising at least 54 carbon atoms in total; and/or
  (4) wherein the at least one small molecule biomarker whose decrease in concentration is compared to the control is a triglyceride having acyl side chains comprising less than 54 carbon atoms in total; and/or
  (5) wherein the at least one small molecule biomarker whose increase in concentration is compared to the control is adipic acid.

In an embodiment the method for assessing whether a subject is at risk to develop or is suffering from ovarian cancer further comprises determining from said sample at least one additional small molecule biomarker wherein an increase in concentration of said biomarker, when compared to a control sample, is indicative of said subject suffering from or having an increased risk of developing ovarian cancer;
  (a) wherein the at least one additional small molecule biomarker whose increase in concentration is compared to the control is selected from the group consisting of hydroxyacids and adipic acid; and/or
  (b) wherein the at least one additional small molecule biomarker whose increase in concentration is compared to the control is selected from the group consisting of hydroxybutyric acids and ketone bodies.

In an embodiment the method for assessing whether a subject is at risk to develop or is suffering from ovarian cancer comprises carrying out determination of any one of items (1), (2), (3), (4), (5); or any one of items (1), (2), (3), (4), (5), and any one of items (a) or (b).

In another embodiment items (1), (2), (a) and (b); items (1), (2), (3), (a) and (b); or items (1) to (5), (a) and (b) are determined. Using several small molecule biomarkers increases reliability of the assessment compared to using only one small molecule biomarker.

In an embodiment the method further comprises determining the level of a protein biomarker for ovarian cancer in blood, such as CA-125 or HE4, and wherein increased protein biomarker together with the presently identified small molecule biomarker determination is indicative for the subject to have an increased risk of developing or suffering from ovarian cancer. Thus, the presently identified biomarkers can be used in combination with CA-125 biomarker to improve reliability of the determination by combining analysis of both at least one small molecule biomarker and CA-125 biomarker. CA-125 can be determined using any method known in the art. Preferably, the determination of CA-125 is from the same sample as used for determining the small molecule biomarker.

In an embodiment an ovarian cancer protein marker, such as CA-125 or HE4, and 3-hydroxybutyric acid are determined and wherein an increase in concentration of the protein biomarker and 3-hydroxybutyric acid is indicative of increased risk of developing or suffering from ovarian cancer. The combined analysis enhances specificity and sensitivity of CA-125 protein biomarker for early and late stage ovarian cancer screening and prognosis. Combined analysis of CA-125 and 3-hydroxybutyric acid is particularly useful for early stage ovarian cancer.

According to the second aspect of the invention there is provided a method of assessing whether a subject has a decreased survival prognosis for ovarian cancer comprising measuring the level of at least one small molecule biomarker in a sample from the subject, wherein
  an increase in the level of the at least one small molecule biomarker, relative to the level of the corresponding small molecule biomarker in a control sample, is indicative that the subject has a poor survival prognosis for the ovarian cancer, and wherein the at least one small molecule biomarker is selected from the group consisting of dihydroxybutyric acids, trihydroxybutyric acid, hydroxyacids, adipic acid, hydroxybutyric acids, and ketone bodies; and/or
  a decrease in the level of the in the at least one small molecule biomarker, relative to the level of the corresponding small molecule biomarker in a control sample, is indicative that the subject has a poor survival prognosis for the ovarian cancer, and wherein the at least one small molecule biomarker is selected from the group consisting of sphingomyelins.

Reliable prognosis for a subject suffering from ovarian cancer is important when the evaluation and decision for the different types of treatments and their duration for the cancer patient are made. In addition, the prognosis affects the intensity of the follow-up after the treatments. Finally, giving as accurate as possible estimate on the prognosis of the disease is important for the patients and their well-being.

According to the third aspect of the invention there is provided an in vitro method for assessing the success rate of ovarian cancer tumor removal in a subject having received tumor therapy, comprising measuring the level of at least one small molecule biomarker in a blood sample from the subject, wherein an increase or decrease in the level of the in the at least one small molecule biomarker, relative to the level of the corresponding small molecule biomarker in a control sample, is indicative that the tumor removal was successful, and
  (1) wherein the at least one small molecule biomarker whose decrease in concentration is compared to the control is selected from the group consisting of dihydroxybutyric acids and trihydroxybutyric acid; and/or (2) wherein the at least one small molecule biomarker whose increase in concentration is compared to the control is selected from the group consisting of sphingomyelins; and/or
(3) wherein the at least one small molecule biomarker whose decrease in concentration is compared to the control is a long chain triglyceride having acyl side chains comprising at least 54 carbon atoms in total; and/or
(4) wherein the at least one small molecule biomarker whose increase in concentration is compared to the control is a triglyceride having acyl side chains comprising less than 54 carbon atoms in total; and/or
(5) wherein the at least one small molecule biomarker whose decrease in concentration is compared to the control is adipic acid.

In an embodiment the method for assessing the success rate of an ovarian cancer tumor removal further comprises determining from said sample at least one additional small molecule biomarker wherein a decrease in concentration of said biomarker, when compared to a control sample, is indicative that the tumor removal was successful;
(a) wherein the at least one additional small molecule biomarker whose decrease in concentration is compared to the control is selected from the group consisting of hydroxyacids and adipic acid; and/or
(b) wherein the at least one additional small molecule biomarker whose decrease in concentration is compared to the control is selected from the group consisting of hydroxybutyric acids and ketone bodies.

In an embodiment the method for assessing the success rate of an ovarian cancer tumor removal comprises carrying out determination of items (1), (2), (a) and (b), or items (1) to (5), (a) and (b).

Monitoring the tumor removal success is an important aspect of treatment and it provides valuable information about the need for further operations or treatment. Accordingly, treatment may be followed by further operations or drug therapy based on the result from the above assessment.

According to the fourth aspect of the invention there is provided an in vitro method of evaluating effectiveness of ovarian cancer therapy in a subject comprising
determining from a sample from said subject the concentration of at least one small molecule biomarker, wherein an increase or decrease in concentration of said sample, when compared to a control sample, is indicative of effectiveness of said therapy;
(1) wherein the at least one small molecule biomarker whose concentration is compared to the control is selected from the group consisting of dihydroxybutyric acids and trihydroxybutyric acid; and/or
(2) wherein the at least one small molecule biomarker whose concentration is compared to the control is selected from the group consisting of sphingomyelins; and/or
(3) wherein the at least one small molecule biomarker whose concentration is compared to the control is long chain triglyceride having acyl side chains comprising at least 54 carbon atoms in total; and/or
(4) wherein the at least one small molecule biomarker whose concentration is compared to the control is a triglyceride having acyl side chains comprising less than 54 carbon atoms in total; and/or
(5) wherein the at least one small molecule biomarker whose concentration is compared to the control is adipic acid;
(a) wherein the at least one additional small molecule biomarker whose concentration is compared to the control is selected from the group consisting of dihydroxyacids and adipic acid; and/or
(b) wherein the at least one additional small molecule biomarker whose decrease in concentration is compared to the control is selected from the group consisting of hydroxybutyric acids and ketone bodies;
and wherein said increase in at least one of (1), (3), (5), (a) and (b), or decrease in (2) or (4), is indicative of ineffective treatment; and/or
decrease in at least one of (1), (3), (5), (a) and (b), or increase in (2) or (4), is indicative of effective treatment.

In the method the effectiveness of the therapy is monitored by following the presently identified small molecule biomarkers. The selected biomarkers reflect the progress of the ovarian cancer and approach the concentration determined for the control sample when the cancer responds to said therapy. Accordingly, therapy may be tailored based on the subject such that only therapy which shows positive response, and is thus found effective, is continued, and therapy which shows no response, and is thus found ineffective, is discontinued.

In an embodiment of the in vitro method of evaluating effectiveness of ovarian cancer therapy in a subject, the small molecule biomarker is 3-hydroxybutyric acid and additionally CA-125 is determined, wherein increase in either of 3-hydroxybutyric acid or CA-125 is indicative of ineffective treatment and decrease in either of 3-hydroxybutyric acid or CA-125 is indicative of effective treatment.

In an embodiment the therapy may comprise any therapeutic treatment typically given to a subject having ovarian cancer, such as, but not limited to, chemotherapy, radiation therapy, hormonal therapy, anti-angiogenic therapy, therapies targeting homologous recombination deficiency, antibody therapy or other targeted therapy utilizing ovarian cancer specific signalling pathways. The treatment may comprise treatment having a direct effect on the metabolism of the malignant tissue. Ovarian cancer therapy may comprise administering a pharmaceutical agent affecting lipid metabolism.

According to a fifth aspect of the invention there is provided an in vitro method of determining the concentration of a metabolite in ovarian tissue of a subject comprising
determining the concentration of the metabolite in a blood sample obtained from the subject;
comparing the blood concentration of the metabolite with the concentration in a control sample wherein an increase in the level of the in metabolite compared to the control sample is indicative that the subject has increased concentration of the metabolite in ovarian tissue;
and wherein the metabolite is selected from the group consisting of a 3-hydroxybutyric acid, 2-hydroxybutyric acid, 3,4-dihydroxybutyric acid, SM(d18:1/21:0), SM(d18:1/14:0), adipic acid, 4-hydroxyphenyllactic acid, 2,4-dihydroxybutyric acid, 3-hydroxyisovaleric acid, 2,3-dihydroxybutyric acid.

In an embodiment the concentration of the metabolite which is determined in ovarian tissue is selected from the group consisting of 2-hydroxybutyric acid and/or 3-hydroxybutyric acid.

The determination of the biomarkers is typically performed using an assay. The assay can be performed with various chemical and high-resolution analytical techniques, as appropriate.

Suitable analytical techniques according to the present methods include, but are not limited to mass spectrometry (MS) and nuclear magnetic resonance (NMR). Any high-resolution technique capable of resolving individual small molecule biomarkers can be used to collect the information on the biomarker in question, such as the concentration of biomarker profile from the biological sample, such as blood serum, plasma, tissue, urine or saliva. Preferably, the information is collected using mass spectrometry. The MS analysis can be coupled to another high performance separation method, such as gas chromatography (GC), two-dimensional gas chromatography (GC×GC), liquid chromatography (LC), high performance liquid chromatography (HPLC) or ultra performance liquid chromatography (UPLC).

The sample from the subject and the control sample may be a blood serum sample, a plasma sample, a saliva sample or a urine sample. Blood serum and plasma samples are preferred. The sample can be prepared with techniques well known in the art. Alternatively, both the sample from the subject and the control sample may also be tissue samples, e.g., ovarian tissue sample.

According to certain embodiments, the methods of the invention provide for measuring the levels of small molecule biomarkers in a plasma sample or a serum sample without the need to isolate or enrich exfoliated tumor cells in said sample prior to detection. In one embodiment, the sample is a non-sedimented sample. In another embodiment, the plasma sample is substantially free of residual cells. In yet another embodiment the blood sample is treated with clot activators and serum is separated by centrifugation, optionally followed by freezing and thawing, prior to analysis.

In another embodiment before the mass spectrometric analysis the small molecule biomarkers of the sample are extracted with a solvent or a solvent mixture from the sample.

Suitable solvents include organic solvents such as methanol, chloroform/methanol or other similar solvents.

In another embodiment the small molecule biomarkers are derivatized before mass spectrometric analysis. In an embodiment the derivatization comprises extraction with an organic solvent, evaporation of the solvent under reduced pressure, and derivatization.

In another embodiment the sample is filtered before determining the small molecule biomarkers by using a filter which removes cells. In an embodiment a filter having a cut-off value of 30 kDa is used to remove cells. In yet another embodiment a filter is used which removes proteins. In an embodiment the sample is reconstituted after the filtering.

In another embodiment the sample or the reconstituted sample is diluted prior to determining the small molecule biomarkers. In an embodiment the sample is diluted at least 1:2 before determining the small molecule biomarkers.

In another embodiment to the sample is added preservative or an internal mass standard.

The small molecule ovarian cancer biomarkers of the present invention allow for easy, reliable and early prediction of ovarian cancer. This will facilitate e.g. earlier intervention, less symptom development and suffering and decreased morbidity. The present biomarkers also allow easy monitoring of the progress of the ovarian cancer as the analysis can be performed on serum samples without the need of collecting a tissue sample.

In certain embodiments the ovarian cancer is an early stage ovarian cancer.

The hydroxyacids as small molecule ovarian cancer biomarkers preferably comprise at least one compound selected from the group consisting of 4-hydroxyphenyllactic acid, and 3-hydroxyisovaleric acid.

The dihydroxybutyric acids as small molecule ovarian cancer biomarkers preferably comprise at least one compound selected from the group consisting of 2,4-dihydroxybutyric acid, 3,4-dihydroxybutyric acid and 2,3-dihydroxybutyric acid.

The trihydroxybutyric acid as small molecule ovarian cancer biomarkers preferably comprise at least one compound selected from the group consisting of 2,3,4-trihydroxybutyric acid.

The sphingomyelins as small molecule ovarian cancer biomarkers is preferably selected from sphingomyelins having d18:1 sphingoid base, optionally having an amide-linked fatty acid with 14-24 carbon atoms and 0-1 double bonds. Even more preferably the sphingomyelin is selected from the group consisting of SM(d18:1/14:0), SM(d18:1/20:1), SM(d18:1/21:0), SM(d18:1/22:0), SM(d18:1/22:1), SM(d18:1/23:0), SM(d18:1/24:0).

The hydroxybutyric acids and ketone bodies as small molecule ovarian cancer biomarkers preferably comprise compounds selected from the group consisting of 2-hydroxybutyric acid, 3-hydroxybutyric acid, acetone and acetoacetic acid.

The long chain triglycerides as small molecule ovarian cancer biomarkers comprise compounds having total acyl chain length of at least 54 carbon atoms.

The short chain triglycerides as small molecule ovarian cancer biomarkers comprise compounds having total acyl chain length of not more than 53 carbon atoms.

The control may be a concentration determined from a single healthy individual or a subject with benign tumor or other medical condition causing similar symptoms to ovarian cancer, or the same subject before developing malignant tissue. The control may also be a sample that represents a combination of samples from a generalised population of healthy individuals. Alternatively, the control may be a set of data concerning the biomarker in a sample previously determined, calculated or extrapolated, or may have yet to be determined, calculated or extrapolated, or may also be taken from the literature.

When 3-hydroxybutyric acid, 2-hydroxybutyric acid, 3,4-dihydroxybutyric acid, 2,4-dihydroxybutyric acid, 2,3-dihydroxybutyric acid, SM(d18:1/21:0), SM(d18:1/14:0), adipic acid, 4-hydroxyphenyllactic acid and 3-hydroxyisovaleric acid were analysed from serum samples as biomarkers for ovarian cancer, the inventor surprisingly found that their concentration follows the concentration determined in the cancer tissue. Thus, it is possible to determine the concentration of these compounds in the ovarian tissue by determining their concentration in the blood serum. Being able to determine concentration of said biomarkers inside tumor by using samples from blood serum has the advantage of monitoring the metabolism within the tumor directly from the blood sample. This can help in monitoring the size of the tumor and metastases in the body without imaging or surgery. In addition, the small molecular metabolites can be used as markers for the treatment efficacy, and how various treatment options affect the metabolism of the tumor cells.

According to the sixth aspect there is provided an in vitro screening method for assessing whether a subject is at risk to develop or is suffering from ovarian cancer comprising determining the concentration of volatile organic compounds (VOC) in breath, wherein an increase in concentration of VOC in breath when compared to a control sample is indicative of said subject suffering from or having an increased risk of developing ovarian cancer.

Volatile organic compounds, such as acetone, can be detected for example by mass spectrometric methods, sensor arrays and electronic noses, laser absorption spectroscopy or ion mobility spectrometry, and, for instance, it has been reported that healthy persons should have acetone levels below 0.9 ppm in their breath. The present inventor has identified in body fluids small molecule biomarkers for ovarian cancer that can be volatile or in chemical reactions converted to volatile compounds, and thus, also be detected from breadth due to their tendency to move to exhaled air in lungs e.g. from blood. Thus any volatile biomarker according to the invention, such as acetone, having a measured level in breath of a subject that is higher than the level measured for a control is indicative of increased risk of developing ovarian cancer.

In an example embodiment the at least one small molecule biomarker whose increase in concentration is compared to the control is selected from the group consisting of 2,4-dihydroxybutyric acid, 3,4-dihydroxybutyric acid, 2,3-dihydroxybutyric acid, 2,3,4-trihydroxybutyric acid, 4-hydroxyphenyllactic acid, 3-hydroxyisovaleric acid, adipic acid, 2-hydroxybutyric acid, 3-hydroxybutyric acid, acetoacetic acid and acetone.

In an example embodiment the at least one small molecule biomarker whose decrease in concentration is compared to the control is selected from the group consisting of SM(d18:1/14:0), SM(d18:1/20:1), SM(d18:1/21:0), SM(d18:1/22:0), SM(d18:1/22:1), SM(d18:1/23:0) and SM(d18:1/24:0).

In an example embodiment the above methods comprises determining the concentration of 1, 2, 3, 4, 5, 6, 7, 8, 9, 10 or more small molecule biomarkers selected from the group consisting of the biomarkers listed above in items (1)-(5), (a) and (b).

In an example embodiment the biomarker concentration is determined by using mass spectrometry, nuclear magnetic resonance spectroscopy, fluorescence spectroscopy or dual polarisation interferometry, an immunoassay, enzymatic assay, colorimetric assay, fluorometric assay, a rapid test, a breath test and/or with a binding moiety capable of specifically binding the biomarker.

In another aspect there is provided use of a pharmaceutical for treating ovarian cancer or one or more of its complications in a subject in need thereof, the method comprising using an effective pharmaceutical for ovarian cancer treatment, wherein the effectiveness of treatment with the pharmaceutical is evaluated using the above method according to the fourth aspect of the invention for evaluating effectiveness of treatment.

In an example embodiment the drug is administered at a dose which causes the concentration of the at least one small molecule ovarian cancer biomarker in the tumor to change from the initial level towards the concentration in the control sample, and wherein the concentration of the at least one small molecule ovarian cancer biomarker is determined using the method according to the above methods.

EXAMPLES

The following examples are provided to illustrate various aspects of the present invention. They are not intended to limit the invention, which is defined by the accompanying claims.

Example 1. Materials and Methods

Description of Study Cohorts and Samples

The serum samples were collected from preoperative primary ovarian cancer patients as well as from patients without ovarian cancer at the Charité Medical University (Berlin, Germany) between September 2000 and February 2011. The Ethics Committee approved the use of the samples for the study. The patient's informed consent was obtained prior to surgery or during subsequent treatment, sample collection and documentation of clinical and surgical data. A validated documentation system was used to record the surgical data. The study population without ovarian cancer consisted of a group of patients with benign tumors, endometriosis, uterus myomatosus, adnexitis and other conditions causing similar symptoms to ovarian cancer. Blood was collected within the Tumor Bank Ovarian Cancer project (http://toc-network.de) using serum tubes containing clot activators (Vacutainer, BD, Medical-Pharmaceutical System, Franklin Lakes, N.J.). Collected blood was clotted for 30 min to 2 h at room temperature and serum was separated by centrifugation at 1200 g for 15 minutes. Serum was aliquoted and stored at −80° C.

Tumor tissue samples were collected at the time of surgery and immediately frozen in liquid nitrogen within 15 minutes of the removal and then stored at −80° C. All tissue samples underwent histopathological assessment to verify histological subtype and high tissue quality, and only specimens presenting adequate tumor area were included in the metabolomic and lipidomic analyses.

GC×GC-TOF Method

Tumor samples were prepared by homogenizing 3-4 mg of tissue with Retsch homogenizer (3 min, 20 Hz). The samples were homogenized into 0.9% NaCl, and the volume was adjusted to get concentration of 0.05 mg/μl. 400 μl methanol and 5 μl standard mixture (valine-d8 (37.6 mg/l), heptadecanoic acid (186.5 mg/l), succinic acid-d4 (62.9 mg/l)) was added to 70 μl of the homogenate. For the serum samples 400 μl methanol and 10 μl standard mixture (valine-d8 (37.6 mg/l), heptadecanoic acid (186.5 mg/l), succinic acid-d4 (62.9 mg/l), glutamic acid-d5 (103.5 mg/l)) was added to 30 μl of the sample. The samples were vortexed for 2 min. After 30 minutes at room temperature the samples were centrifuged for 5 min at 10000 rpm. 200 μl of the supernatant was moved to a GC vial and evaporated to dryness under nitrogen. The samples were derivatized with 25 μl (MOX) (45° C., 60 min) and 25 μl (MSTFA) (45° C., 60 min) and 50 μl of hexane with retention index compounds and injection standard (4,4'-dibromooctafluorobiphenyl) was added to samples.

For the analysis, a Leco Pegasus 4D GC×GC-TOFMS instrument (Leco Corp., St. Joseph, Mich.) equipped with a cryogenic modulator was used. The GC part of the instrument was an Agilent 6890 gas chromatograph (Agilent Technologies, Palo Alto, Calif.), equipped with split/splitless injector. The first-dimension chromatographic column was a 10-m Rxi-5MS capillary column with an internal diameter of 0.18 mm and a stationary-phase film thickness of 0.18 μm, and the second-dimension chromatographic column was a 1.5 m BPX-50 capillary column with an internal diameter of 100 μm and a film thickness of 0.1 μm. A methyl deactivated retention gap (1.5 m×0.53 mm i.d.) was used in the front of the first column. High-purity helium was used as the carrier gas at a constant pressure mode (40 psig). A 4-s separation time was used in the second dimension. The MS spectra were measured at 45-700 amu with 100 spectra/sec. For the injection, a splitless injection (1.0 μl) at 240° C. was utilized. The temperature program was as follows: the first-dimension column oven ramp began at 50° C. with a 2 min hold after which the temperature was programmed to 240° C. at a rate of 7° C./min and further to 300° C. at a rate of 25° C./min and then held at this temperature for 3 min. The second-dimension column temperature was maintained 15° C. higher than the corresponding first-dimension column. The programming rate and hold times were the same for the two columns.

ChromaTOF vendor software (LECO) was used for within-sample data processing, and in-house made software Guineu (Castillo et al., 2011, Anal Chem) was used for alignment, normalization and peak matching across samples. The peaks were first filtered based on number of detected peaks in the total profile of all sample runs. The normalization for uncalibrated metabolites was performed by correction for internal standard C17:0. 27 of the metabolites were checked manually in each serum sample and 29 metabolites in each tumor tissue sample for correct integration and identification. Other mass spectra from the GC×GC-TOFMS analysis were searched against NIST05 mass spectral library.

LC-MS Method

Tumor samples were prepared by homogenizing 2-3 mg of tissue with Retsch homogenizer (3 min, 20 Hz). The samples were homogenized into 0.9% NaCl, and the volume was adjusted to get concentration of approximately 0.05 mg/µl. The samples were extracted with chloroform:methanol (2:1; 250 µl) after adding an internal standard mixture with Cer(d18:1/17:0), PC(17:0/0:0), PC(17:0/17:0), PE(17:0/17:0) and TG(17:0/17:0/17:0) at concentration level of 0.5-1 µg/sample. The samples were vortexed for 2 min, incubated 30 min at RT and centrifuged at 7800 g for 3 min. A labelled lipid standard mixture containing PC(16:1-D3/0:0), PC(16:1/16:1-D6) and TG(16:0/16:0/16:0-1303) at concentration level of 0.5 µg/sample was added into the separated lipid extracts (100 µl) before UPLC-MS analysis.

10 µl of serum samples were used for the analyses, and the samples were prepared by adding an internal standard mixture with DG(17:0/17:0/0:0), CE(19:0), Cer(d18:1/17:0), MG(17:0/0:0/0:0), PA(17:0/17:0), PC(17:0/0:0), PC(17:0/17:0), PE(17:0/17:0), PG(17:0/17:0) and TG(17:0/17:0/17:0) at concentration level of 0.2 µg/sample and extracting with chloroform:methanol (2:1, 100 µl). The samples were vortexed for 2 min, incubated 30 min at RT and centrifuged at 7800 g for 3 min. A labelled lipid standard mixture containing PC(16:1-D3/0:0), PC(16:1/16:1-D6) and TG(16:0/16:0/16:0-1303) at concentration level of 0.1 µg/sample was added into the separated lipid extracts (60 µl) before UPLC-MS analysis Lipid extracts from tumor and serum samples were analysed on a Waters Q-Tof Premier mass spectrometer combined with an Acquity Ultra Performanc LC™ (UPLC™). The column was an Acquity UPLC™ BEH C18 2.1×100 mm with 1.7 µm particles. The solvent system included A) water (1% 1 M NH$_4$Ac, 0.1% HCOOH) and B) acetonitrile/isopropanol (1:1, 1% 1M NH$_4$Ac, 0.1% HCOOH). The gradient started from 65% A/35% B, reached 80% B in 2 min, 100% B in 7 min and remained there for the next 7 min. There was a 5 min re-equilibration step before the following run. The flow rate was 0.400 ml/min and the injected amount 1.0 µl. Reserpine was used as the lock spray reference compounds. The lipid profiling was performed using ESI in positive mode, and the data were collected at a mass range of m/z 300-1200 with scan duration of 0.2 sec.

The data were processed using MZmine 2 software (http://mzmine.sourceforge.net/) and the processing included alignment of peaks, peak integration, normalization, and peak identification. Lipid identification was based on an internal spectral library. The data were normalized using internal standards representative for the class of lipid present in the samples: the intensity of each identified lipid was normalized by dividing it with the intensity of its corresponding standard and multiplying it by the concentration of the standard. All monoacyl lipids except cholesterol esters, such as monoacylglycerophospholipids, were normalized with PC(17:0/0:0), all diacyl lipids except ethanolamine phospholipids were normalized with PC(17:0/17:0), all ceramides with Cer(d18:1/17:0), all diacyl ethanolamine phospholipids with PE(17:0/17:0), triacylglycerols with TG(17:0/17:0/17:0), and cholesterol esters with ChoE(19:0) in the serum and TG(17:0/17:0/17:0) in the tissue samples. Other (unidentified) molecular species were normalized with PC(17:0/0:0) for retention time <300 s, PC(17:0/17:0) for retention time between 300 s and 410 s, and TG(17:0/17:0/17:0) for higher retention times. The tumor samples were normalized with the weight of the sample.

Statistical Analyses

The data from the GC×GC-TOF method were obtained for 100 subjects without malignant disease (control group) as well as for 158 ovarian cancer patient serum samples. In addition, the data from tumor tissue analysis were obtained for 112 ovarian cancer patients having matching serum samples. The results from the LC-MS method were obtained for 100 subjects without malignant disease as well as for 158 ovarian cancer patient serum samples. In addition, the data from tumor tissue analysis were obtained for 134 ovarian cancer patients having matching serum samples. CA-125 data was available for the serum samples of 145 ovarian cancer patients and 73 subjects without malignant disease.

All statistical analyses were performed using R, version 3.1.0. For the two-group comparisons unpaired t-tests and fold changes were calculated after log 2 transformation of the data. In case there were zero values in the data, the data was imputed with a value corresponding to the half of the minimum value of the corresponding molecule across all samples. The association of the small molecules to survival was investigated by Kaplan-Meier plots with a median split and logrank test. In addition, Cox proportional hazards regression test was performed for each small molecule with and without incorporating the tumor reduction information into the model. The predictive models for the ovarian cancer diagnosis from serum with small molecules were binary logistic regression models. For cross-validation, the dataset was 1000 times split randomly into training set (comprising ⅔ of the samples), and the constructed model was tested in the validation set (comprising ⅓ of the samples). For the analysis of stage I-II tumors no cross validation was performed.

The small molecule biomarkers from tumor tissue and serum samples from LC-MS and GC×GC-TOF-MS data were matched using the RANSAC alignment method, which has been implemented in the MZmine 2 (Pluskal et al., 2010, BMC Bioinformatics) and the in-house developed Guineu software (Castillo et al., 2011, Anal Chem).

Example 2. Results

Information on the Selected Biomarker Molecules

The GC×GC-TOF-MS data contained 497 metabolite peaks and the LC-MS data 635 lipid peaks. In this patent application the example results are shown for the most interesting selected metabolites, listed in Table 1. The molecules were selected based on the results from the statistical analyses, chemical structures and biological significance of the compounds.

In some cases GCxGC-TOF-MS data may contain several peaks that are having same identification. This may be due to analytical reasons or e.g. stereoisomeric structures. In cases where the GCxGC-TOF-MS analysis included a reference standard compound, always the peak corresponding to the standard compound was selected as the final result.

For 2,3-dihydroxybutyric acid and 2,3,4-trihydroxybutyric acid reference compounds were not included in the analysis. For these molecules the peak showing statistically significant result both in the malignant vs. benign comparison as well as in the survival analysis was selected as an example.

TABLE 1

Mass spectrometric details of the molecules for which the example results are shown. For the molecules obtained from the LC-MS method retention time (s) and m/z values are shown. For the molecules obtained from the GCxGC-TOF-MS method retention index (RTI) and spectrum are shown.

| Small molecules | Method | RT(I) | m/z | Spectrum |
|---|---|---|---|---|
| *1. Di- and trihydroxybutyric acids* | | | | |
| 2,4-Dihydroxybutyric acid | GCxGC-TOF-MS | 1434.5 | — | 73:998, 103:822, 45:259, 147:187, 55:169, 75:128, 129:120, 219:116, 59:111, 133:84, 104:70, 74:68, 131:59, 101:43, 47:41, 220:34, 105:31, 72:28, 149:28, 58:27, 148:26, 203:25, 130:23, 115:20, 57:18, 61:17, 85:14, 102:14, 177:12, 66:11, 221:10, 46:9, 134:9, 60:8, 87:8, 189:8, 119:7, 175:7, 321:7, 77:6, 135:6, 56:5, 71:5, 52:4, 132:4, 190:4, 51:3, 79:3, 99:3, 204:3, 50:2, 53:2, 70:2, 89:2, 49:1, 67:1, 88:1, 116:1, 159:1 |
| 3,4-Dihydroxybutyric acid | GCxGC-TOF-MS | 1453.9 | — | 73:998, 45:194, 147:147, 75:133, 74:78, 117:74, 133:73, 59:72, 189:71, 101:57, 233:42, 47:41, 129:36, 191:28, 149:26, 231:25, 72:24, 55:21, 103:21, 148:21, 58:20, 89:20, 203:20, 157:19, 85:18, 131:18, 61:16, 202:15, 246:13, 190:12, 46:10, 57:10, 66:9, 119:9, 115:8, 134:8, 234:7, 60:6, 71:6, 118:6, 135:6, 204:6, 321:6, 76:5, 217:5, 99:4, 205:4, 232:4, 52:3, 70:2, 87:2, 102:2, 51:1, 53:1, 77:1, 79:1, 88:1, 130:1, 159:1, 192:1 |
| 2,3-Dihydroxybutyric acid | GCxGC-TOF-MS | 1888 | — | 73:998, 117:265, 147:145, 45:120, 75:103, 74:76, 292:50, 143:42, 131:37, 129:32, 133:29, 59:27, 118:25, 148:20, 189:19, 219:19, 333:17, 130:16, 102:15, 72:13, 103:13, 293:13, 149:12, 119:11, 217:11, 305:10, 115:9, 101:7, 191:7, 204:7, 221:7, 220:6, 231:6, 55:5, 58:5, 77:5, 277:5, 294:5, 47:4, 144:4, 171:4, 46:3, 110:3, 134:3, 271:3, 334:3, 52:2, 51:1, 61:1, 76:1, 79:1, 116:1, 132:1, 190:1, 314:1 |
| 2,3,4-Trihydroxybutyric acid | GCxGC-TOF-MS | 1575.7 | — | 73:998, 147:265, 45:191, 117:102, 74:83, 75:76, 103:75, 102:66, 55:58, 292:58, 130:53, 220:51, 59:48, 133:48, 205:43, 148:41, 217:37, 131:27, 149:25, 129:24, 57:21, 47:19, 72:19, 221:18, 58:17, 89:17, 143:15, 293:15, 83:13, 71:12, 46:11, 101:11, 118:9, 189:9, 104:8, 119:8, 177:8, 61:7, 206:7, 294:7, 66:6, 85:6, 115:6, 204:6, 218:6, 134:5, 207:5, 222:5, 291:5, 56:4, 70:4, 132:4, 53:3, 105:3, 52:2, 60:2, 77:2, 87:2, 219:2, 99:1, 191:1, 245:1 |
| *2. Sphingomyelins* | | | | |
| SM(d18:1/14:0) | LC-MS | 306.5 | 675.5444 | |
| SM(d18:1/20:1) | LC-MS | 373.4 | 757.6235 | |
| SM(d18:1/21:0) | LC-MS | 416.8 | 773.6545 | |
| SM(d18:1/22:0) | LC-MS | 429.1 | 787.6705 | |
| SM(d18:1/22:1) | LC-MS | 401.8 | 785.6540 | |
| SM(d18:1/23:0) | LC-MS | 442.1 | 801.6868 | |
| SM(d18:1/24:0) | LC-MS | 453.9 | 815.7023 | |
| *3. Hydroxyacids and adipic acid* | | | | |
| 4-Hydroxyphenyllactic acid | GCxGC-TOF-MS | 1925.5 | — | 73:998, 179:451, 45:238, 147:146, 74:81, 75:80, 180:66, 308:52, 119:42, 133:27, 149:27, 59:26, 148:21, 47:20, 91:20, 181:18, 293:17, 131:13, 163:13, 309:13, 46:11, 72:10, 135:10, 193:10, 58:9, 82:9, 177:9, 77:8, 105:7, 61:6, 89:6, 115:6, 281:6, 55:4, 66:4, 90:4, 219:4, 76:3, 102:3, 103:3, 191:3, 292:3, 294:3, 310:3, 355:3, 65:2, 151:2, 161:2, 51:1, 52:1, 53:1, 57:1, 60:1, 68:1, 70:1, 71:1, 78:1, 79:1, 83:1, 101:1, 104:1, 117:1, 134:1 |
| 3-Hydroxyisovaleric acid | GCxGC-TOF-MS | 1220.3 | — | 73:925, 131:657, 75:636, 147:555, 45:300, 47:194, 115:131, 74:89, 148:85, 61:84, 144:73, 95:71, 132:70, 55:62, 149:49, 77:45, 85:45, 76:42, 58:36, 247:35, 59:33, 46:30, 66:29, 83:25, 60:24, 113:23, 204:23, 205:23, 133:21, 57:18, 80:17, 101:17, 116:17, 53:15, 72:14, 48:13, 50:13, 52:13, 49:12, 62:12, 79:12, 51:11, 203:11, 69:10, 145:10, 151:10, 56:9, 71:9, 99:9, 102:9, 117:9, 218:9, 54:7, 84:6, 87:6, 129:6, 163:6, 189:6, 78:5, 81:5, 96:5, 119:5, 150:5, 219:5, 248:5, 82:4, 114:4, 157:4, 63:3, 67:3, 105:3, 134:3, 136:3, 153:3, 154:3, 206:3, 88:2, 90:2, 100:2, 103:2, 118:2, 120:2, 130:2, 135:2, 164:2, 226:2, 64:1, 65:1, 68:1, 70:1, 91:1, 92:1, 97:1, 98:1, 104:1, 106:1, 112:1, 121:1, 127:1, 128:1, 137:1, 138:1, 143:1, 146:1, 158:1, 159:1, 161:1, 165:1, 175:1, 191:1, 221:1, 227:1, 254:1 |

TABLE 1-continued

Mass spectrometric details of the molecules for which the example results are shown. For the molecules obtained from the LC-MS method retention time (s) and m/z values are shown. For the molecules obtained from the GCxGC-TOF-MS method retention index (RTI) and spectrum are shown.

| Small molecules | Method | RT(I) | m/z | Spectrum |
|---|---|---|---|---|
| Adipic acid | GCxGC-TOF-MS | 1516.4 | — | 75:997, 73:555, 111:504, 55:480, 45:285, 83:266, 141:190, 147:178, 47:176, 129:85, 61:77, 172:76, 74:71, 185:66, 76:63, 56:58, 159:45, 69:43, 149:41, 275:33, 59:32, 112:30, 67:29, 72:29, 77:29, 99:29, 58:25, 133:25, 142:25, 148:23, 157:23, 86:21, 130:18, 46:16, 60:16, 143:16, 53:14, 84:13, 85:13, 217:13, 155:12, 204:12, 173:10, 57:8, 113:8, 117:8, 186:8, 131:7, 115:6, 54:5, 70:5, 81:5, 276:5, 48:4, 51:4, 68:4, 89:4, 200:4, 49:3, 52:3, 62:3, 66:3, 79:3, 82:3, 87:3, 132:3, 139:3, 160:3, 100:2, 101:2, 118:2, 119:2, 145:2, 150:2, 156:2, 158:2, 50:1, 63:1, 71:1, 88:1, 96:1, 97:1, 102:1, 105:1, 134:1, 135:1, 146:1, 227:1 |
| 4. Hydroxybutyric acids and ketone bodies | | | | |
| 2-Hydroxybutyric acid | GCxGC-TOF-MS | 1145 | — | 73:997, 131:493, 147:433, 45:291, 75:187, 59:107, 66:96, 74:89, 133:76, 148:68, 47:67, 132:56, 81:55, 149:39, 205:39, 58:38, 61:33, 55:32, 57:28, 72:23, 190:23, 115:22, 46:19, 233:18, 101:16, 69:15, 117:14, 60:13, 77:12, 99:12, 143:12, 76:11, 95:11, 103:11, 52:10, 67:10, 85:9, 71:8, 87:8, 134:7, 206:7, 53:6, 130:6, 70:5, 191:5, 51:3, 102:3, 105:3, 116:2, 119:2, 56:1, 129:1 |
| 3-Hydroxybutyric acid | GCxGC-TOF-MS | 1175.5 | — | 73:941, 147:813, 117:505, 75:404, 45:381, 191:273, 88:158, 47:151, 233:140, 148:131, 59:126, 66:107, 74:92, 133:85, 130:73, 149:73, 115:70, 61:68, 118:54, 101:51, 192:50, 72:48, 69:46, 131:45, 58:43, 76:28, 234:28, 119:27, 189:27, 99:26, 46:25, 103:25, 55:24, 204:24, 60:23, 193:23, 57:22, 143:18, 77:17, 89:17, 116:15, 87:14, 56:12, 71:12, 235:12, 67:11, 85:10, 134:10, 102:8, 132:8, 70:7, 105:7, 150:7, 177:7, 48:6, 109:6, 52:5, 53:5, 135:5, 217:5, 51:4, 68:4, 81:4, 190:4, 205:4, 49:2, 62:2, 94:1, 158:1, 218:1 |
| Acetoacetic acid | GCxGC-TOF-MS | 1261.1 | — | 73:890, 147:867, 45:567, 231:367, 75:170, 157:152, 99:135, 148:134, 47:116, 133:98, 69:96, 59:82, 74:77, 149:76, 232:68, 89:60, 58:39, 67:35, 46:34, 61:33, 131:33, 72:32, 115:32, 66:30, 143:30, 77:28, 141:28, 233:28, 113:27, 127:23, 76:20, 156:20, 163:20, 52:19, 55:18, 79:17, 134:17, 71:16, 158:16, 60:15, 57:14, 97:14, 103:13, 51:12, 78:12, 171:12, 85:11, 98:11, 100:11, 173:11, 101:10, 50:9, 53:9, 84:9, 159:9, 82:8, 114:8, 49:7, 126:7, 132:7, 144:7, 70:6, 108:6, 48:5, 83:5, 87:5, 90:5, 119:5, 128:5, 56:4, 62:4, 64:4, 135:4, 150:4, 188:4, 246:4, 112:3, 117:3, 193:3, 215:3, 63:2, 68:2, 91:2, 105:2, 110:2, 129:2, 146:2, 151:2, 172:2, 189:2, 228:2, 54:1, 65:1, 88:1, 93:1, 95:1, 102:1, 116:1, 118:1, 142:1, 145:1, 160:1, 177:1, 184:1, 201:1, 216:1 |

The Concentrations of Small Molecule Biomarkers are Altered in Patients with Ovarian Cancer and Especially in Those with Incomplete Tumor Reduction Table 2 summarizes the results for the selected small molecule biomarkers and, as comparison, for CA-125, a widely used protein biomarker in ovarian cancer diagnostics.

As evident from Table 2 and FIG. 1, all the small molecule biomarkers showed a statistically highly significant difference in their levels in the ovarian cancer patient serum samples when compared to the control subjects having benign tumors and other non-malignant conditions. All the selected molecules were increased in patients with malignant ovarian tumors, except for sphingomyelins that showed an opposite trend. Especially 3,4-dihydroxybutyric acid and 3-hydroxybutyric acid showed low p-values in the order of 1e-27 and 1e-21, respectively, indicating highly significant result.

Figure 2:
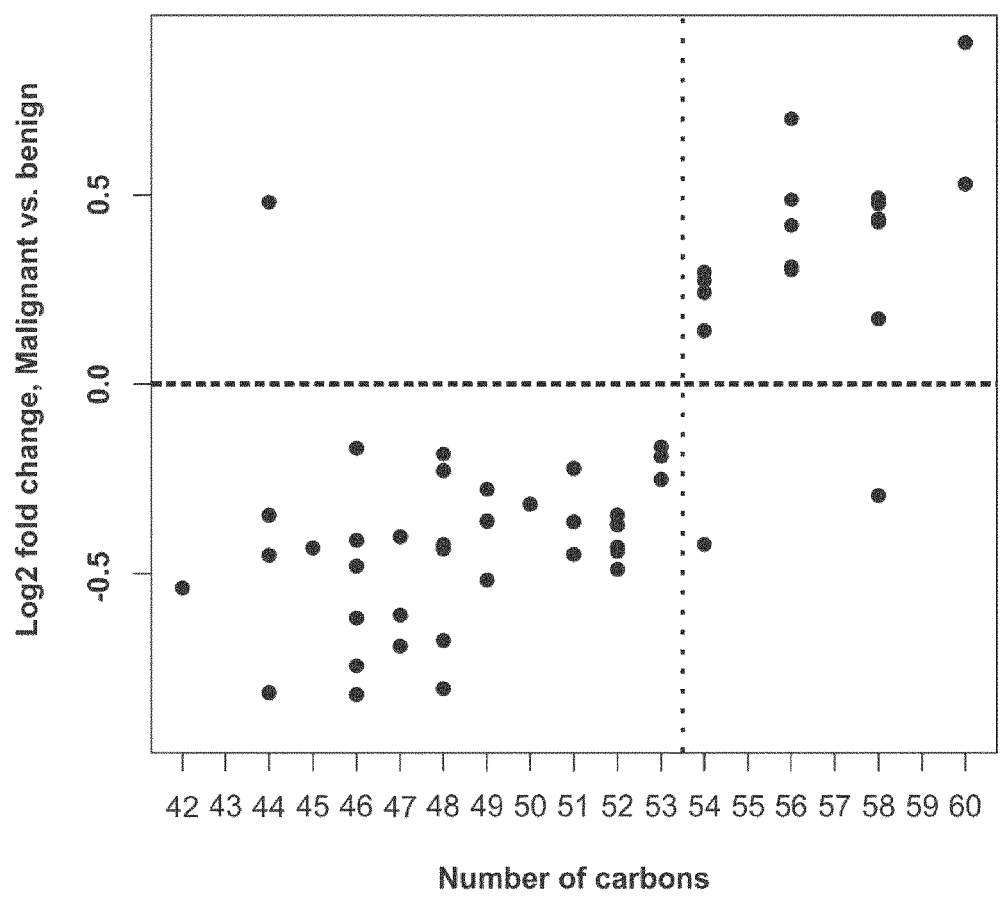
FIG. 2 discloses the change of triacylglycerols (TAGs) in the serum of ovarian cancer patients when compared to the control group. In the plot each dot represents one TAG molecule, which showed a statistically significant result in the t-test between the groups, and the x-axis indicates the total number of carbons in the fatty acyl side chains for each TAG. There is an evident change in the distribution of TAGs in the serum of ovarian cancer patients. With the exception of one lipid, all the TAGs with 53 or less carbons in the fatty acyl side chains are decreased in ovarian cancer patients as compared to subjects without malignant tumor. In contrast, with the exception of two lipids, all the TAGs with 54 or more carbons in the fatty acyl side chains are increased in ovarian cancer patients when compared to the control group.

Also, triacylglycerols (TAGs) showed a change in their levels in the serum of ovarian cancer patients. These lipids presented a trend where those TAGs with 53 or less carbons in their fatty acyl side chains were decreased and those with 54 or more carbons were increased in ovarian cancer patients when compared to the control group (FIG. 2).

In order to investigate whether the small molecule biomarkers are associated with the amount of tumor mass in the patient, the ovarian cancer patients were divided into two groups, i.e. those having either complete or incomplete tumor reduction during the surgery. This information does not directly provide the size of the tumor, but it is logical that the completeness of the tumor reduction during the surgery is correlated with the tumor mass present in the body. As shown in Table 2, the classical ovarian cancer marker CA-125 did not show statistically significant difference between patients with complete or incomplete tumor reduction. In contrast, especially the small molecules belonging to the di- and trihydroxybutyric acid and sphingomyelin classes showed statistically significant result. Interestingly, a progressive change was observed for di- and trihydroxybutyric acids so that the lowest levels were observed in patients with benign condition and the highest levels in patients with malignant tumor and incomplete tumor reduction (FIG. 2). Exactly the opposite phenomenon was observed for compounds of the sphingomyelin class.

In conclusion, all the small molecule biomarkers as well as CA-125 protein marker showed altered levels in the serum of ovarian cancer patients, but only selected small molecule biomarkers were related to tumor reduction, and thus indirectly to the tumor mass of the patients. Thus, the small molecule biomarkers are reflecting better the size of the tumor than CA-125.

As shown in Table 3, random 3 lipids or metabolites selected 1000 times for the models showed rather low AUC values (mean less than 0.70) and large confidence intervals indicating that only specific small molecule biomarkers are

TABLE 2

Results of statistical analyses for tumor malignancy, tumor reduction and overall survival of the patients.

| | MALIGNANT VS. BENIGN | | TUMOR REDUCTION | | OVERALL SURVIVAL | COX REGRESSION MODELS (STANDARDIZED) | | | | | |
|---|---|---|---|---|---|---|---|---|---|---|---|
| | | | | | | WITHOUT TR | | WITH TR | | | |
| Small molecule/CA-125 | p-value | log2 fc | p-value | log2 fc | p-value | p-value | hazard ratio | p-value | hazard ratio | p-value TR | hazard ratio TR |
| 1. Di- and trihydroxybutyric acids | | | | | | | | | | | |
| 2,4-Dihydroxybutyric acid | 1.05E−03 | 0.28 | 3.59E−03 | 0.35 | 1.17E−02 | 4.95E−01 | 1.06 | 4.30E−01 | 1.07 | 4.81E−04 | 0.58 |
| 3,4-Dihydroxybutyric acid | 5.65E−27 | 0.87 | 2.40E−03 | 0.33 | 2.31E−02 | 1.21E−02 | 1.25 | 1.33E−02 | 1.26 | 5.45E−04 | 0.58 |
| 2,3-Dihydroxybutyric acid | 1.32E−07 | 0.60 | 3.55E−04 | 0.48 | 3.77E−02 | 1.60E−04 | 1.45 | 2.46E−03 | 1.36 | 4.26E−03 | 0.63 |
| 2,3,4-Trihydroxybutyric acid | 2.08E−04 | 0.25 | 1.38E−03 | 0.32 | 6.87E−02 | 1.19E−02 | 1.28 | 1.85E−02 | 1.27 | 7.41E−04 | 0.59 |
| 2. Sphingomyelins | | | | | | | | | | | |
| SM(d18:1/14:0) | 1.80E−06 | −0.34 | 2.57E−02 | −0.21 | 4.64E−01 | 2.39E−02 | 0.77 | 6.43E−02 | 0.80 | 1.54E−03 | 0.61 |
| SM(d18:1/20:1) | 4.24E−06 | −0.26 | 5.36E−02 | −0.14 | 4.32E−02 | 8.60E−02 | 0.83 | 1.58E−01 | 0.85 | 9.15E−04 | 0.59 |
| SM(d18:1/21:0) | 3.78E−11 | −0.53 | 7.30E−04 | −0.36 | 4.00E−04 | 1.03E−03 | 0.67 | 6.41E−03 | 0.71 | 4.17E−03 | 0.63 |
| SM(d18:1/22:0) | 1.12E−11 | −0.47 | 1.12E−01 | −0.15 | 7.20E−03 | 2.24E−02 | 0.78 | 4.35E−02 | 0.80 | 9.97E−04 | 0.60 |
| SM(d18:1/22:1) | 8.51E−13 | −0.48 | 5.74E−03 | −0.21 | 2.52E−02 | 1.26E−02 | 0.75 | 3.68E−02 | 0.78 | 1.76E−03 | 0.61 |
| SM(d18:1/23:0) | 3.54E−12 | −0.54 | 9.81E−04 | −0.32 | 1.24E−02 | 2.81E−04 | 0.65 | 1.81E−03 | 0.69 | 4.78E−03 | 0.64 |
| SM(d18:1/24:0) | 2.18E−15 | −0.64 | 1.26E−02 | −0.24 | 1.62E−02 | 2.55E−02 | 0.76 | 5.37E−02 | 0.79 | 1.22E−03 | 0.60 |
| 3. Hydroxyacids and adipic acid | | | | | | | | | | | |
| 4-Hydroxyphenyllactic acid | 1.55E−02 | 0.22 | 2.80E−03 | 0.31 | 4.00E−04 | 2.60E−05 | 1.41 | 4.56E−04 | 1.34 | 3.02E−03 | 0.62 |
| 3-Hydroxyisovaleric acid | 1.27E−04 | 1.01 | 5.62E−01 | 0.21 | 1.75E−02 | 1.20E−03 | 1.31 | 2.77E−03 | 1.28 | 8.42E−04 | 0.59 |
| Adipic acid | 1.86E−07 | 0.52 | 1.62E−01 | 0.18 | 1.05E−02 | 2.69E−03 | 1.35 | 2.88E−03 | 1.34 | 5.20E−04 | 0.58 |
| 4. Hydroxybutyric acids and ketone bodies | | | | | | | | | | | |
| 2-Hydroxybutyric acid | 4.32E−10 | 0.69 | 1.03E−01 | −0.18 | 4.64E−01 | 5.39E−01 | 0.93 | 9.97E−01 | 1.00 | 6.72E−04 | 0.58 |
| 3-Hydroxybutyric acid | 6.06E−21 | 2.53 | 4.39E−01 | −0.18 | 7.87E−01 | 5.17E−01 | 1.08 | 3.33E−01 | 1.12 | 3.91E−04 | 0.57 |
| Acetoacetic acid | 9.11E−07 | 1.39 | 2.06E−01 | 0.64 | 7.62E−02 | 3.53E−01 | 1.11 | 6.80E−01 | 1.05 | 6.88E−04 | 0.58 |
| CA-125 | 7.25E−52 | 5.01 | 1.12E−01 | 0.68 | 5.13E−01 | 5.65E−01 | 1.06 | 7.29E−01 | 1.04 | 8.11E−04 | 0.58 | log2 fc = log2 fold change,
TR = tumor reduction.
p-values < 0.05 are highlighted in bold.

Predictive Models for Malignant Tumors

Figure 3:
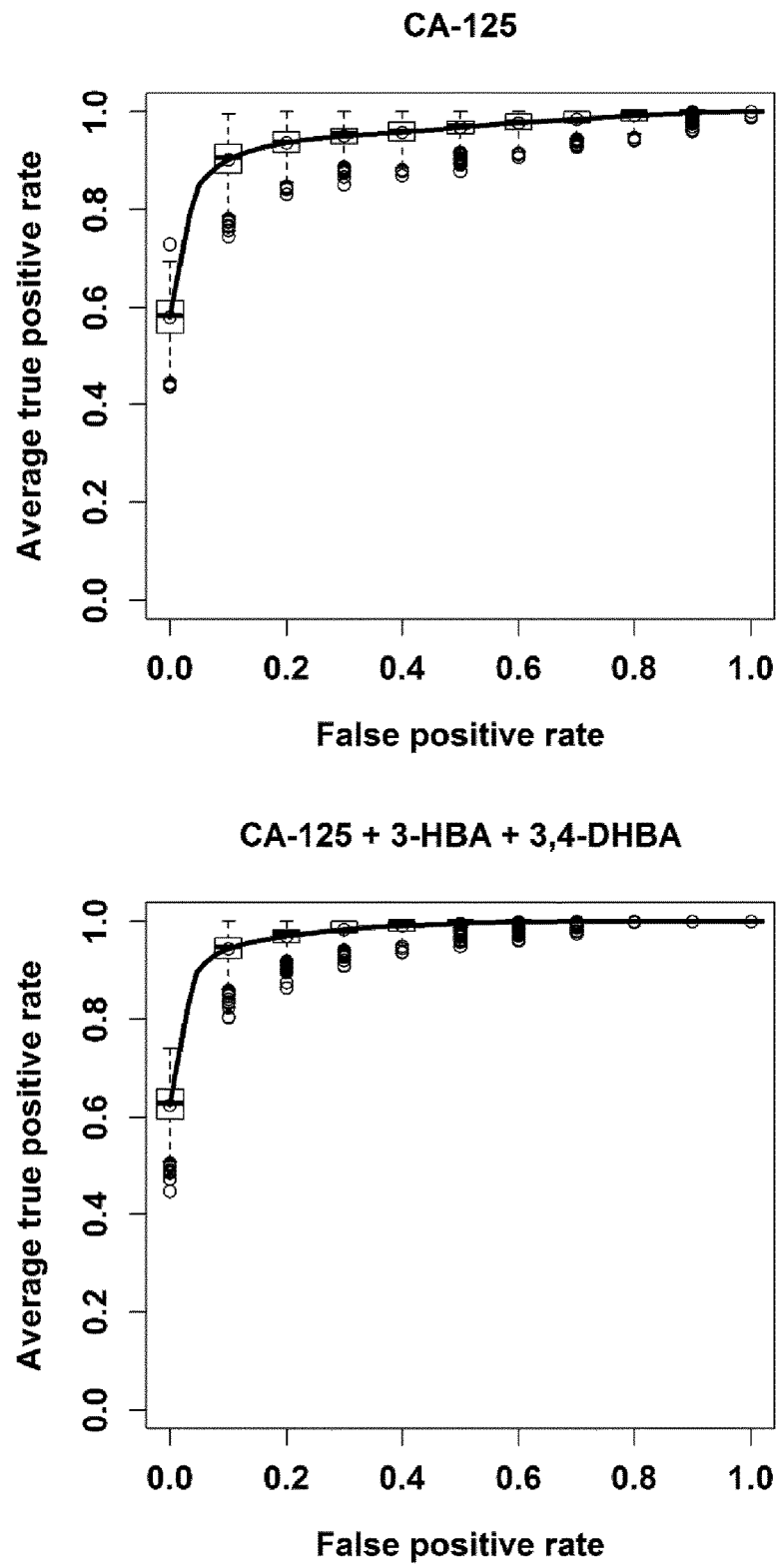
FIG. 3 discloses receiver operating characteristic (ROC) curves when predicting the patients that are having malignant ovarian tumor. The models were cross-validated so that the data set was randomly split 1000 times into training (⅔ of the samples) and validation (⅓ of the samples) sets, and the models constructed in the training set were tested in the validation set. The lines present the mean values, and the boxplots the variability of all the runs. The mean area under the curve (AUC) values and their 95% confidence intervals are presented in Table 3. The plots and the AUC values demonstrated that the highest values and most accurate predictions were achieved, when the models contained CA-125 together with 3-hydroxybutyric acid and 3,4-dihydroxybutyric acid with or without SM(d18:1/24:0) incorporated into the model. CA-125 together with the three SMs shown in the plot yielded a slightly better model than a model incorporating CA-125 only. The conclusion is that incorporating information from small molecule biomarkers to CA-125 concentration increases sensitivity and specificity of the prediction when compared to the information from CA-125 only.
Figure 3:
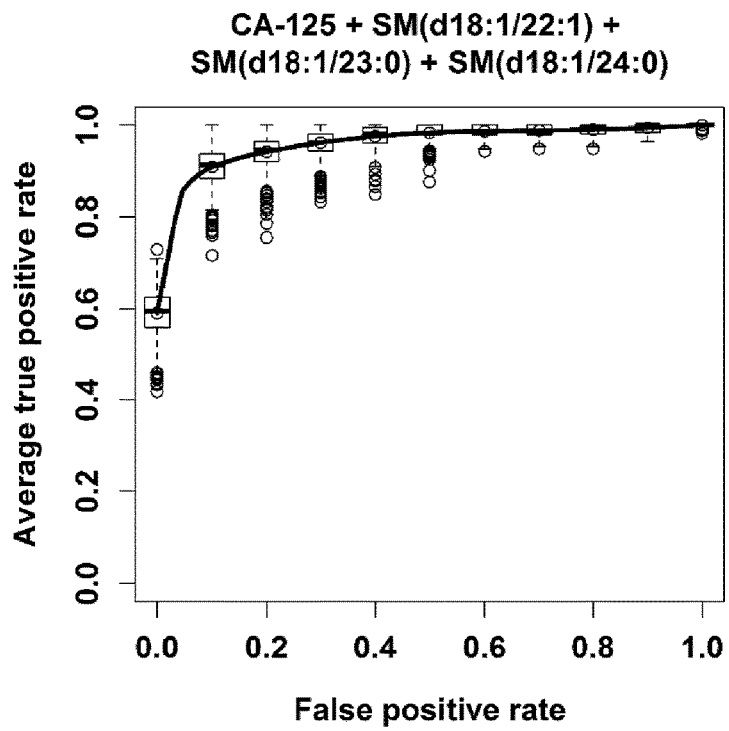
Figure 3:
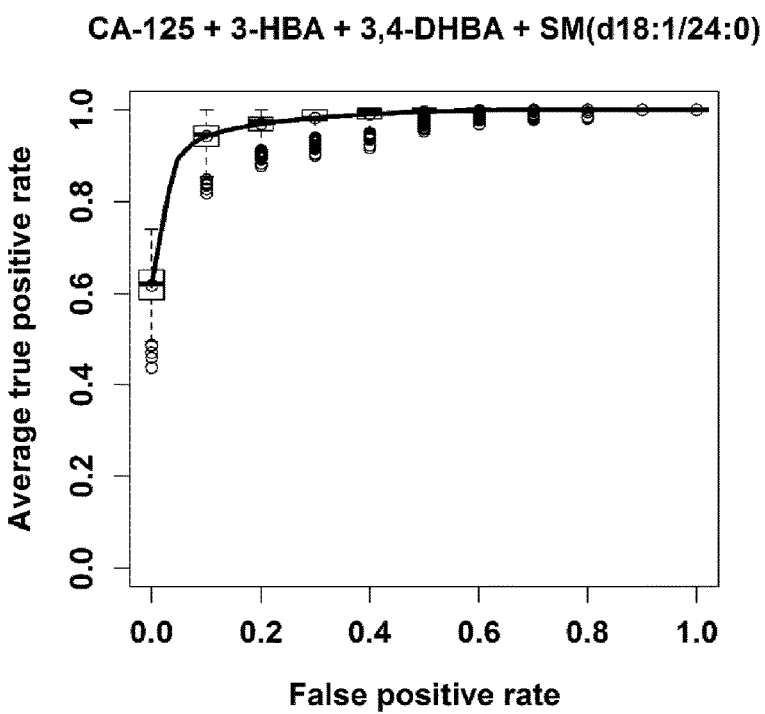

Logistic regression models were constructed to investigate whether the concentration of small molecule biomarkers can be used in predicting which patients are suffering from malignant tumor. For this end, in each case the data was split 1000 times randomly into training set (⅔ of the samples) and the model constructed in the training set was tested in the validation set (remaining ⅓ of the samples). The ROC curves were drawn based on all the 1000 models, and examples for four different cases are shown in FIG. 3. The results for different combinations of small molecule biomarkers and CA-125 are shown in Table 3.

able to predict the patients with malignant ovarian tumors. Three sphingomyelins showed mean AUC value of 0.78, and 3,4-dihydroxybutyric acid together with 3-hydroxybutyric acid showed high mean AUC value of 0.91. CA-125 also showed high mean AUC value of 0.95, but the prediction was even more accurate when either sphingomyelins or butyric acids were incorporated into the model together with CA-125. Especially incorporating 3,4-dihydroxybutyric and 3-hydroxybutyric acids into the model raised the mean AUC value to 0.98, i.e. close to perfect separation of the groups.

TABLE 3

Mean AUC values and 95% confidence intervals for example logistic regression models with different combinations of small molecules and CA-125 protein marker.

| CA-125 | 3,4-DHBA | 3-HBA | SM(d18:1/24:0) | SM(d18:1/22:1) | SM(d18:1/23:0) | 3 random lipids | 3 random metabolites | AUC |
|---|---|---|---|---|---|---|---|---|
| X | X | X | | | | | | 0.98 (0.96, 1.00) |
| X | X | X | X | | | | | 0.98 (0.96, 1.00) |

TABLE 3-continued

Mean AUC values and 95% confidence intervals for example logistic regression models with different combinations of small molecules and CA-125 protein marker.

| CA-125 | 3,4-DHBA | 3-HBA | SM(d18:1/24:0) | SM(d18:1/22:1) | SM(d18:1/23:0) | 3 random lipids | 3 random metabolites | AUC |
|---|---|---|---|---|---|---|---|---|
| X |   | X |   |   |   |   |   | 0.97 (0.95, 0.99) |
| X | X |   |   |   |   |   |   | 0.97 (0.95, 0.99) |
| X |   |   | X | X | X |   |   | 0.96 (0.93, 0.99) |
| X |   |   |   |   |   |   |   | 0.96 (0.92, 0.99) |
|   | X | X | X |   |   |   |   | 0.91 (0.87, 0.95) |
|   | X | X |   |   |   |   |   | 0.91 (0.86, 0.95) |
|   | X |   |   |   |   |   |   | 0.86 (0.80, 0.91) |
|   |   | X |   |   |   |   |   | 0.84 (0.77, 0.90) |
|   |   |   | X | X | X |   |   | 0.78 (0.70, 0.84) |
|   |   |   |   |   |   | X |   | 0.69 (0.51, 0.83) |
|   |   |   |   |   |   |   | X | 0.66 (0.48, 0.85) |

Figure 4:
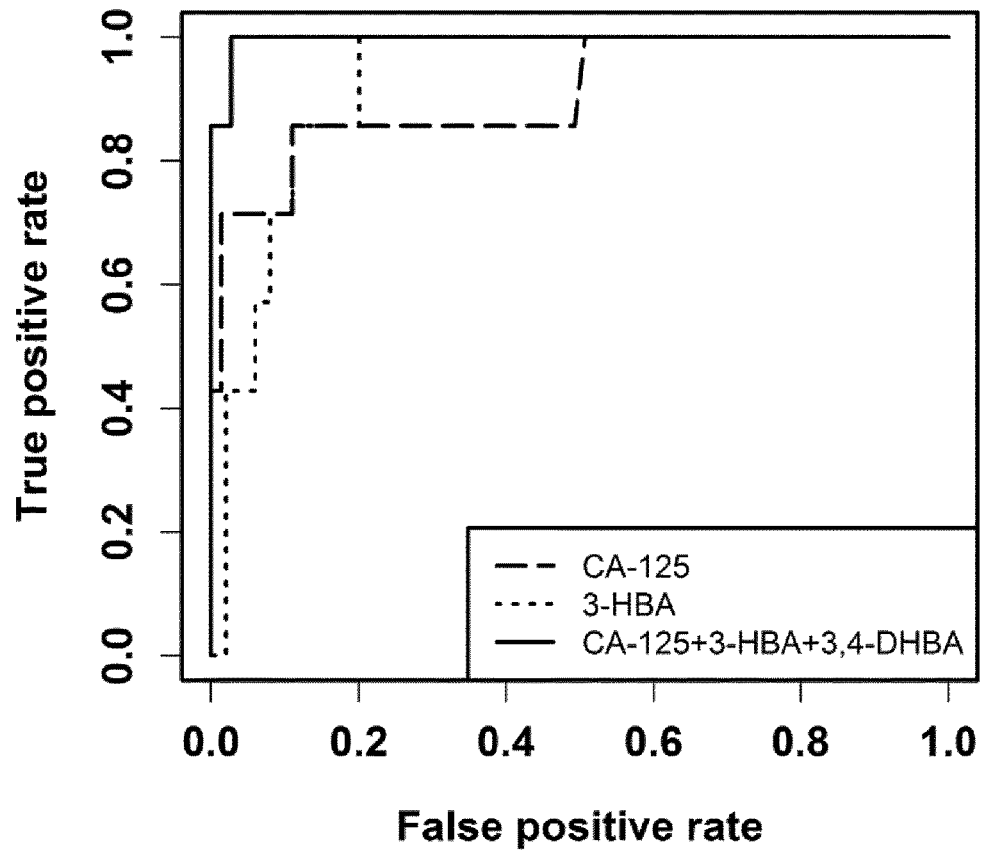
FIG. 4 discloses ROC curves for models classifying the stage I and II patients from control subjects without malignant tumor. The data contained only 7 patients with stage I and II ovarian cancer, and the AUC value for CA-125 for this patient population was higher than expected. However, even despite these limitations, 3-hydroxybutyric acid (3-HBA) showed higher AUC value (all the values are shown in Table 4), and especially a model containing information from CA-125 together with 3-hydroxybutyric acid and 3,4-dihydroxybutyric (3,4-DHBA) acid showed close to perfect separation of the groups. This result gives evidence that the small molecule biomarkers are useful for diagnosing early-stage ovarian cancer patients with or without the information of CA-125 incorporated into the model.
Figure 5:
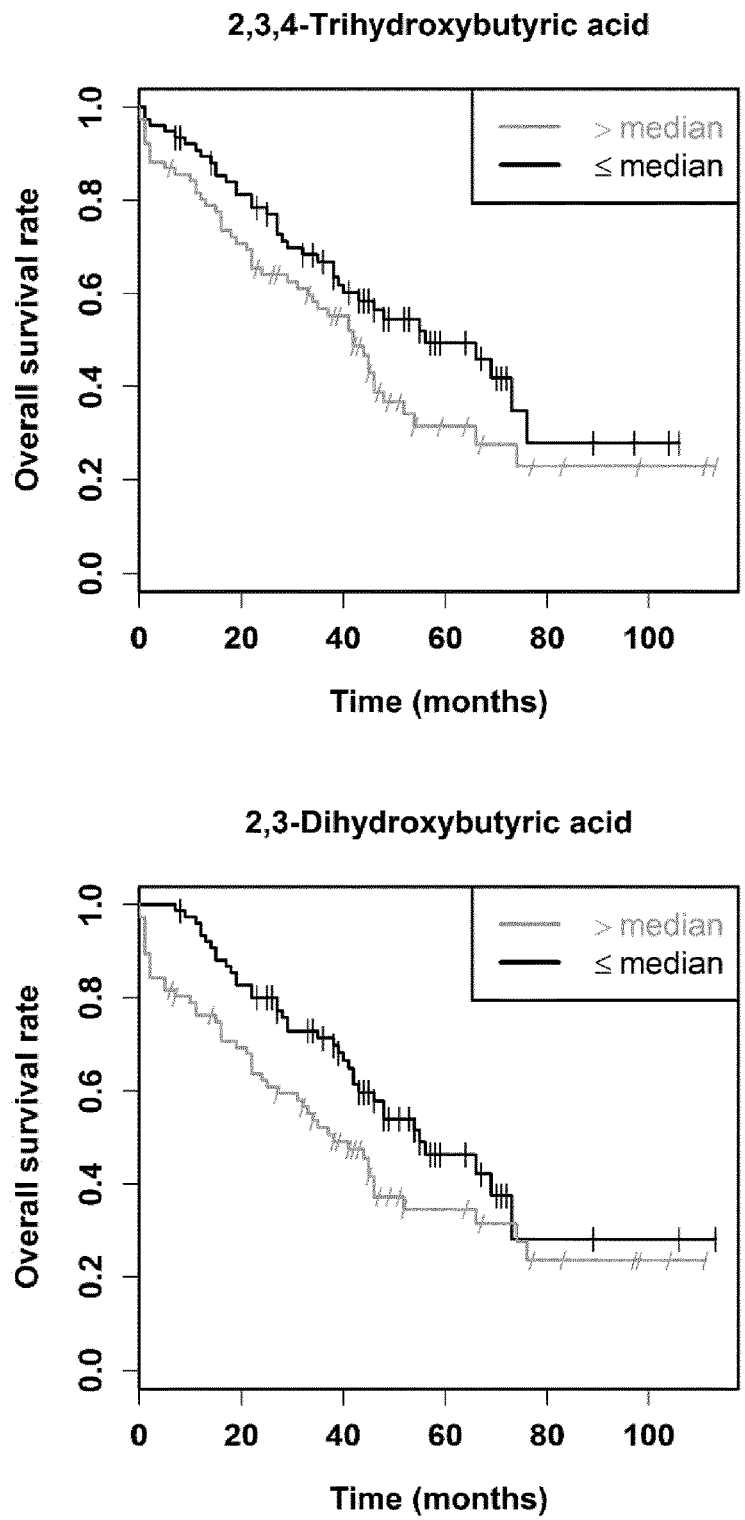
FIG. 5 discloses Kaplan-Meier curves for each small molecule biomarker and CA-125. The plots show the overall survival rates when the patients are divided into two groups for each molecule; those having concentration less than or equal to the median of all samples and those having concentration higher than the median of all samples. The p-values for these results are shown in Table 2. It was evident that for most small molecule biomarkers higher concentration in serum indicated worse overall survival. However, for sphingomyelins (SMs) in general lower concentration in the serum indicated worse overall survival. CA-125 did not show any association to the overall survival of the patients, and thus the small molecule biomarkers were superior prognostic markers as compared to CA-125.
Figure 5:
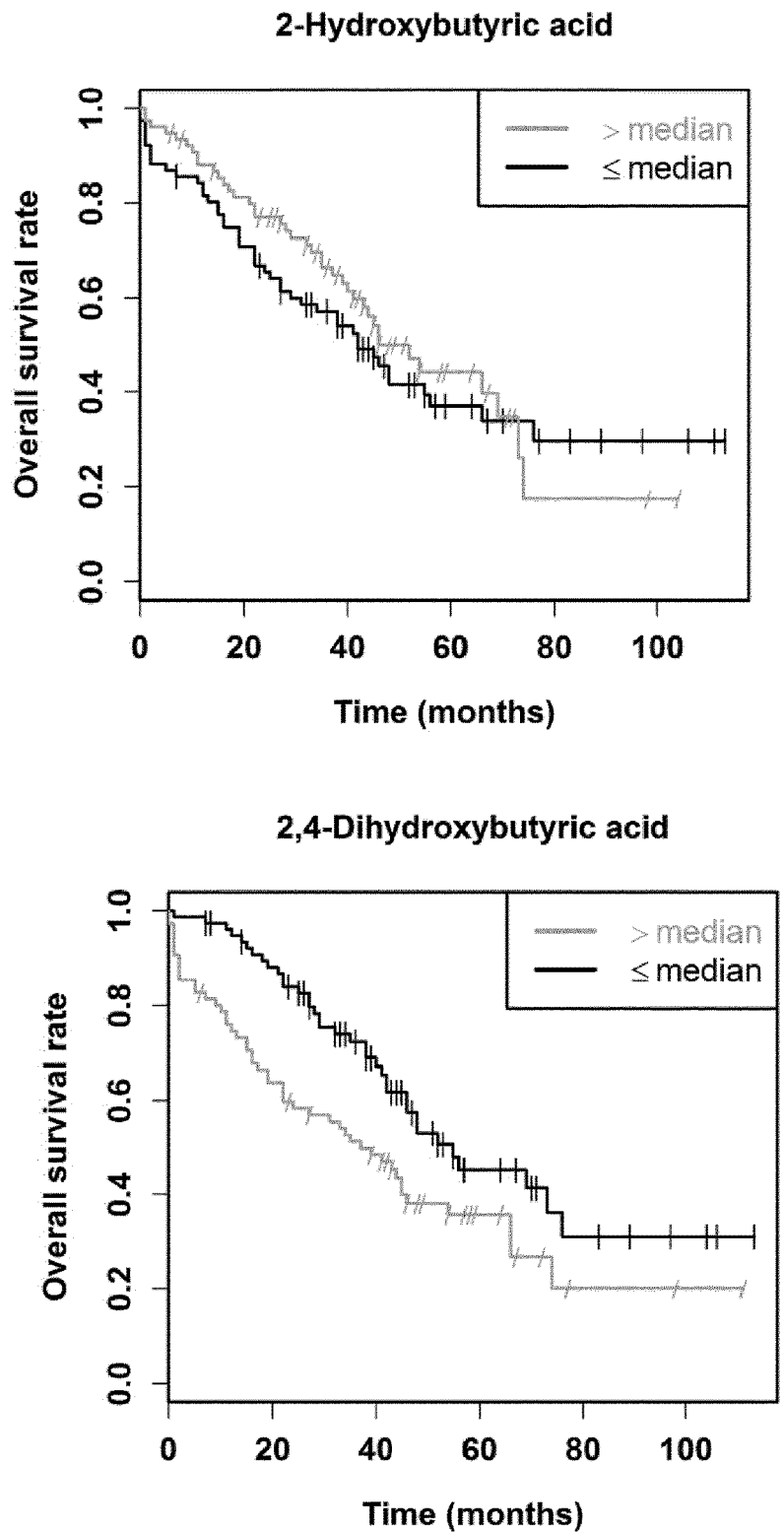
Figure 5:
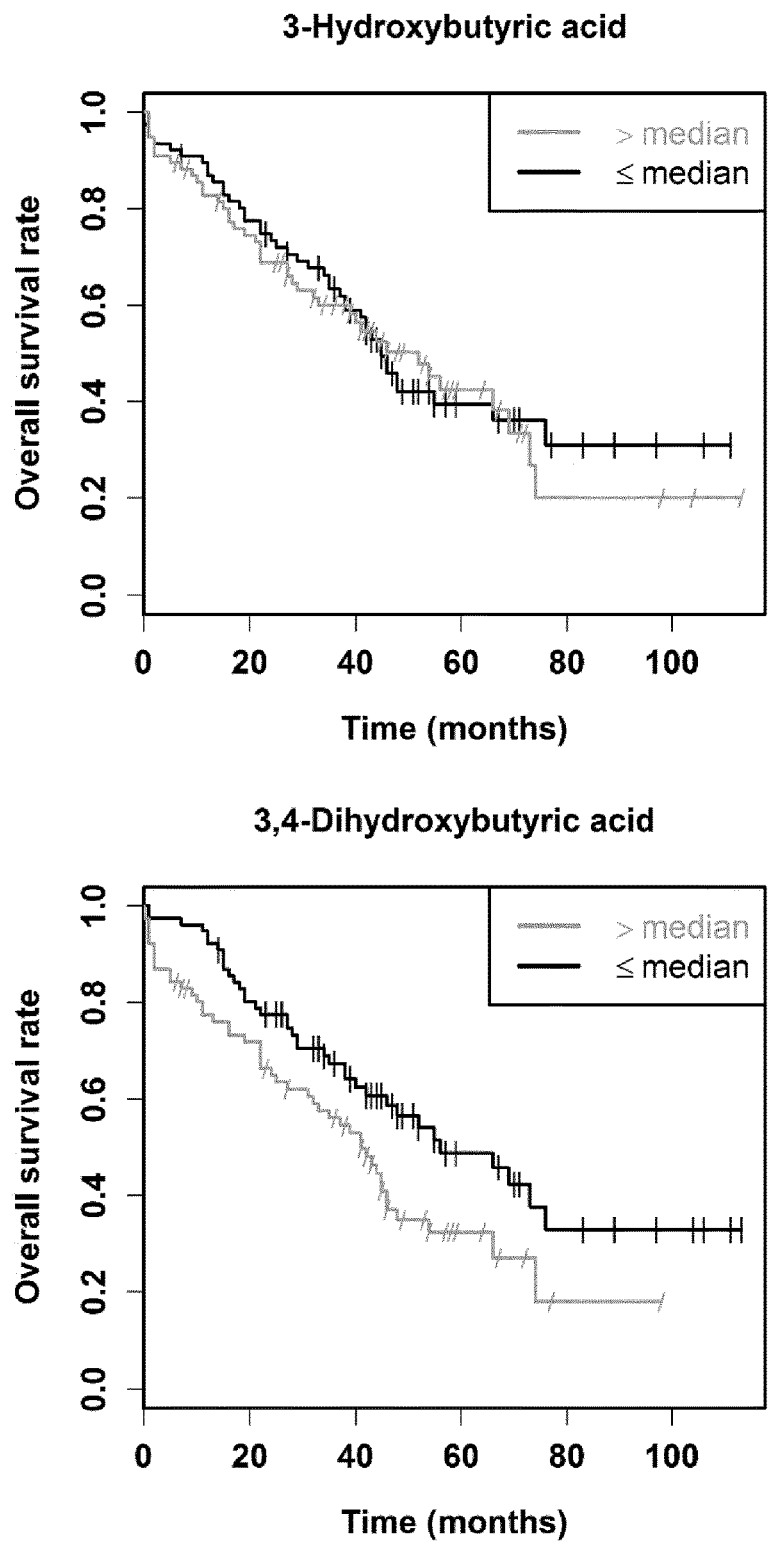
Figure 5:
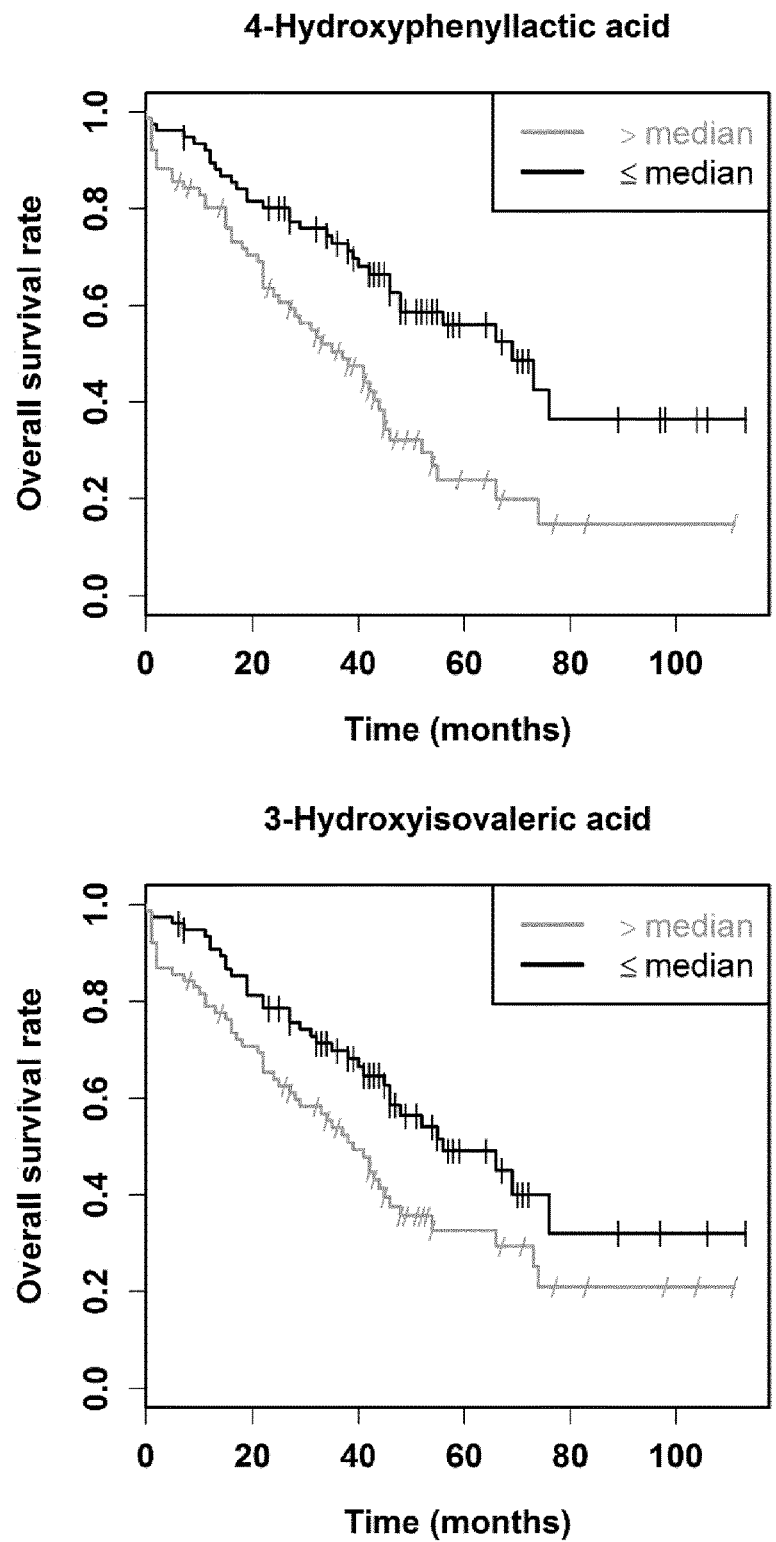
Figure 5:
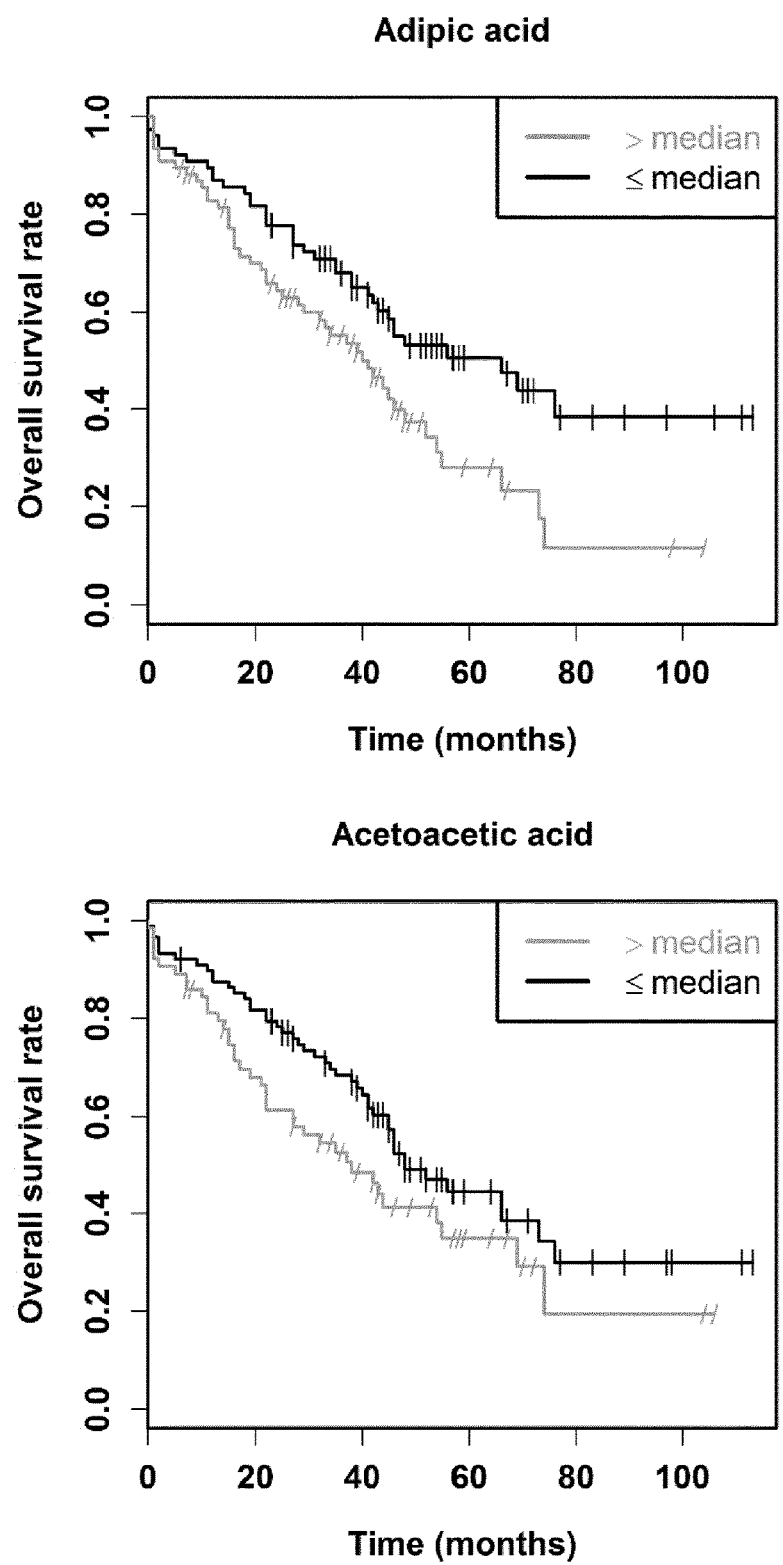
Figure 5:
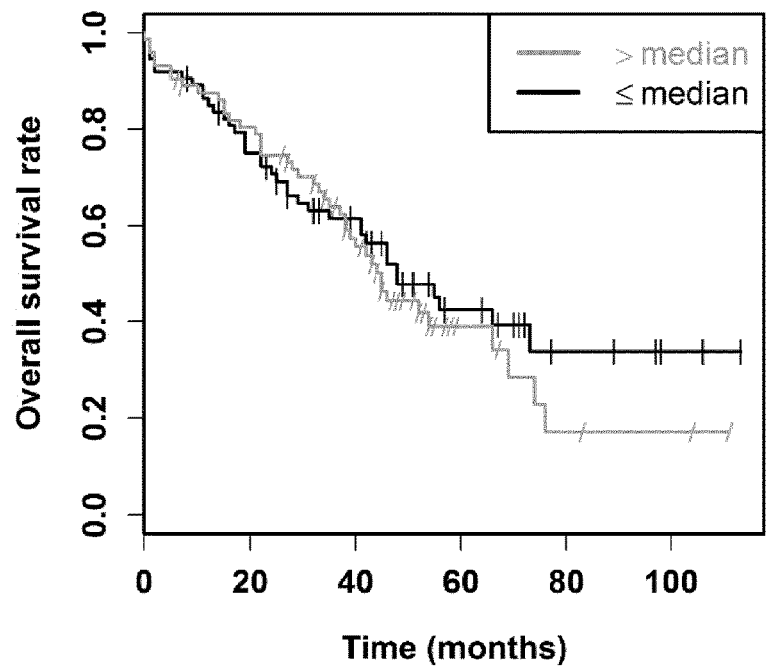
Figure 5:
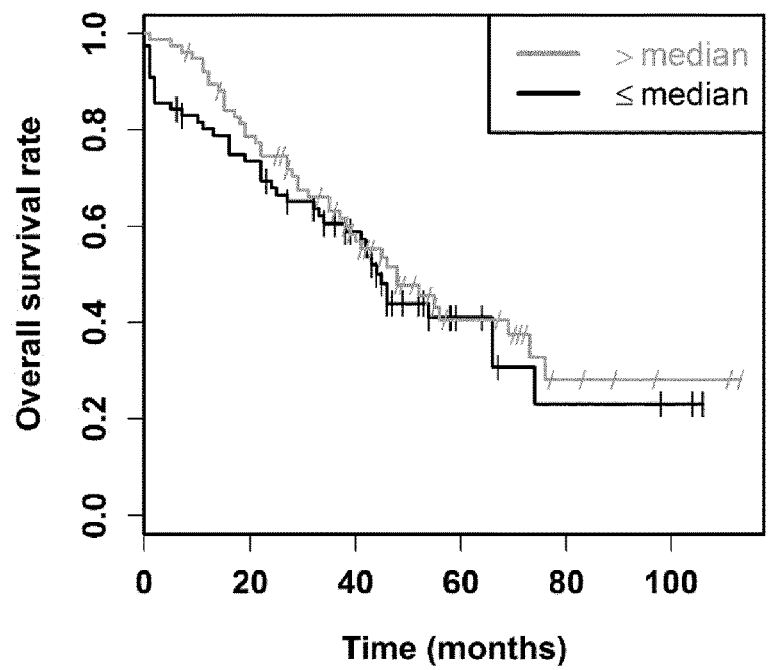
Figure 5:
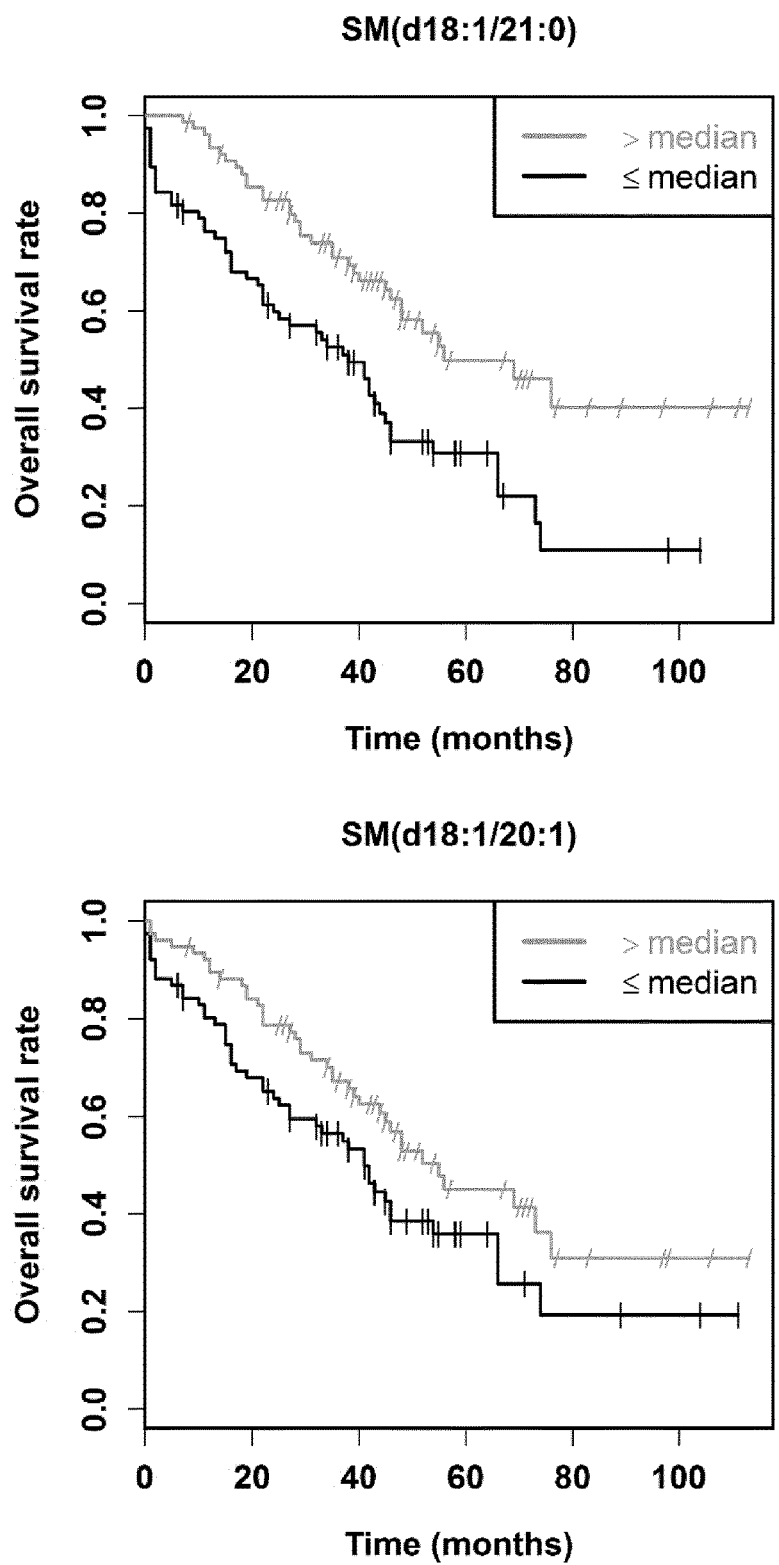
Figure 5:
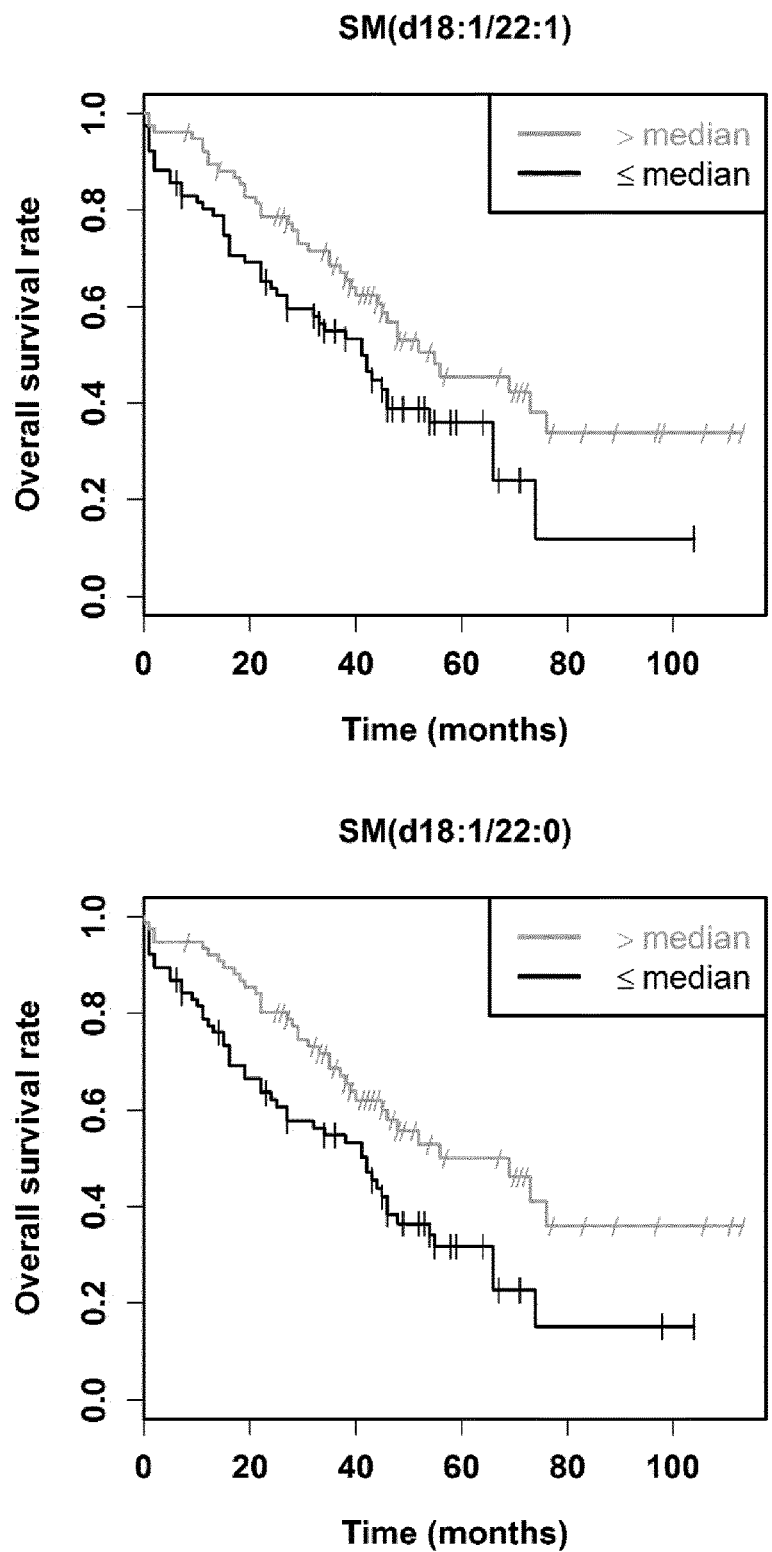
Figure 5:
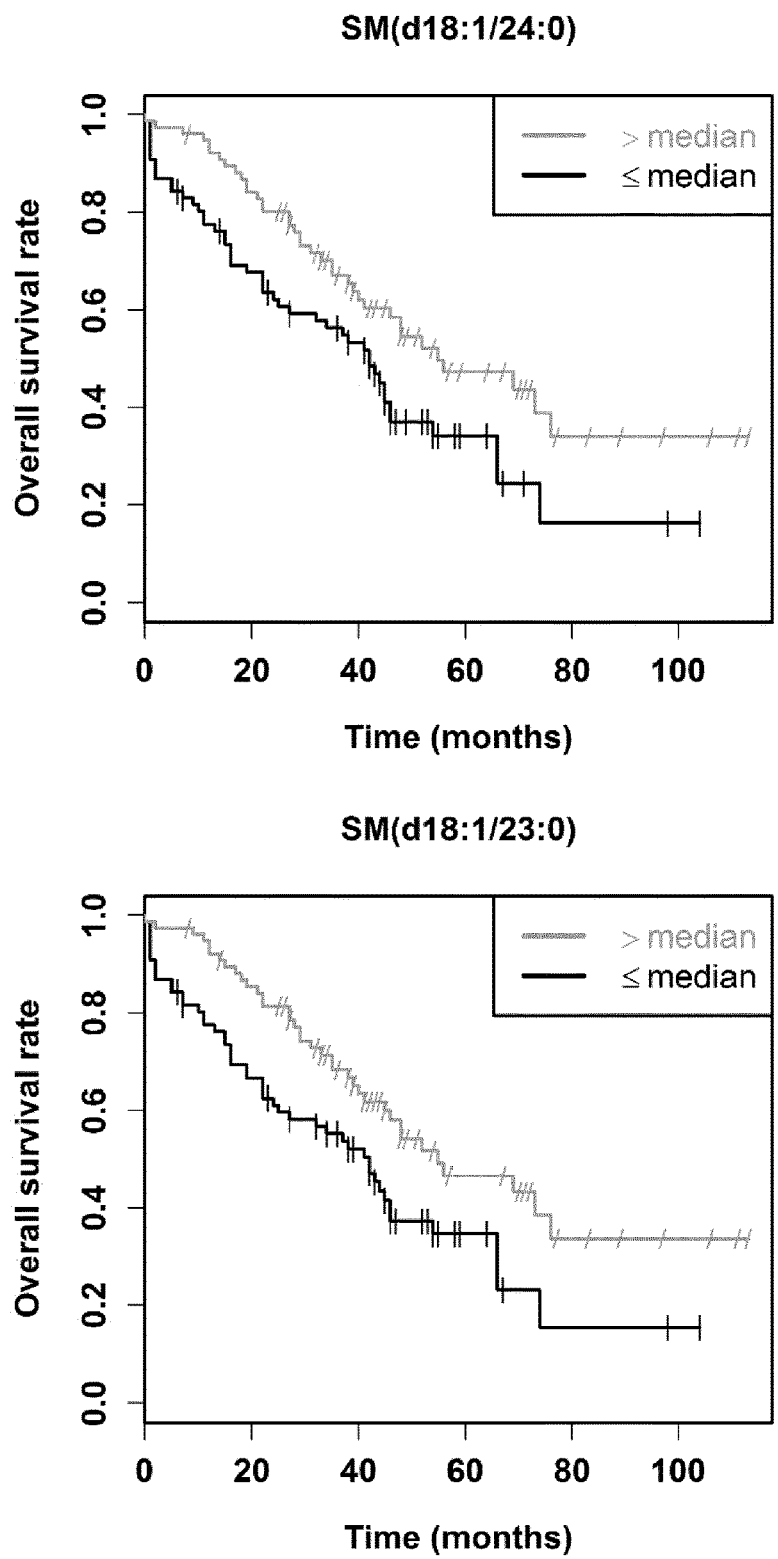

CA-125 protein marker is good in diagnosing late-stage ovarian cancer, but the detection of early-stage ovarian cancer is more challenging. Therefore, new biomarkers for early-stage ovarian cancer would be needed. The population of the present study had only limited number of patients with early stage (I or II) ovarian cancer (n=7). Nevertheless, logistic regression model was constructed in classifying these cases from the control group. The variables included in these example models and their AUC values are presented in Table 4 and visualized in FIG. 4. In this study population CA-125 showed unexpectedly high AUC value of 0.91. Surprisingly, e.g. 3-hydroxybutyric acid alone showed better AUC value of 0.93. Furthermore, the AUC values were increased when one or more small molecular biomarkers were incorporated into the model together with CA-125. Eventually, 3-hydroxybutyric combined with CA-125 showed AUC value of 0.994, and when also 3,4-dihydroxybutyric acid was added to the model, the AUC reached 1.0.

higher or lower concentration of the molecule than the median of all samples. Then, Kaplan-Meier plots were constructed (FIG. 5), and log-rank test was used to calculate p-value for the difference in the overall survival rate between the groups. In this study population CA-125 marker did not show statistically significant result regarding the survival of the patients (Table 2). However, all the small molecules (with the exception of SM(d18:1/14:0) as well as hydroxybutyric acids and ketone bodies) showed a statistically significant result. As evident from FIG. 5 and Table 2, increased concentration of di- and trihydroxybutyric acids, hydroxyacids and adipic acid are associated with worse overall survival. In contrast, lower concentration of sphingomyelins in the serum of the ovarian cancer patients predict worse overall survival for the patients.

It is intuitive that the success of tumor reduction during the surgery is associated with the overall survival of the patients. As many small molecules were found to be asso-

TABLE 4

AUC values for logistic regression models with different combinations of small molecules and CA-125 protein marker.

| CA-125 | 3,4-DHBA | 3-HBA | SM(d18:1/24:0) | SM(d18:1/22:1) | SM(d18:1/23:0) | AUC |
|---|---|---|---|---|---|---|
| X | X | X | X |   |   | 1.00 |
| X | X | X |   |   |   | 1.00 |
| X |   | X |   |   |   | 0.99 |
| X |   |   | X | X | X | 0.95 |
| X | X |   |   |   |   | 0.95 |
|   | X | X | X |   |   | 0.94 |
|   | X | X |   |   |   | 0.93 |
|   |   | X |   |   |   | 0.93 |
| X |   |   |   |   |   | 0.91 |
|   |   |   | X | X | X | 0.64 |

In summary, the small molecule biomarkers outperform CA-125 in diagnosing especially early-stage ovarian cancer, and also show good predictive value in the whole study population. Especially combining one or several biomarkers together with CA-125 it is possible to get models with higher sensitivity and specificity for ovarian cancer diagnosis as compared with CA-125 alone.

Small Molecule Levels are Associated with Overall Survival of the Patients

Next it was investigated whether the small molecule biomarkers are associated with the overall survival of the patients with malignant tumors. To investigate this, for each investigated small molecule and CA-125 protein marker the patients were divided into two groups, those having either ciated with the tumor reduction (and thereby indirectly with tumor burden), it was investigated whether the small molecule biomarkers can predict survival independently from the success of tumor reduction. For this, cox proportional hazards regression models were constructed for each small molecule and CA-125 with and without tumor reduction information incorporated into the model. Interestingly, almost all of the small molecule biomarkers that showed statistically significant result in the Kaplan-Meier analysis, also showed statistically significant result in the cox regression model even though the tumor reduction was incorporated into the model. This means that the small molecules are strong predictors of the overall survival of the patients and can predict the survival independently of the tumor reduction information.

In summary, small molecule biomarkers are associated with the overall survival of the patients, and in contrast to CA-125, show prognostic value.

Figure 6:
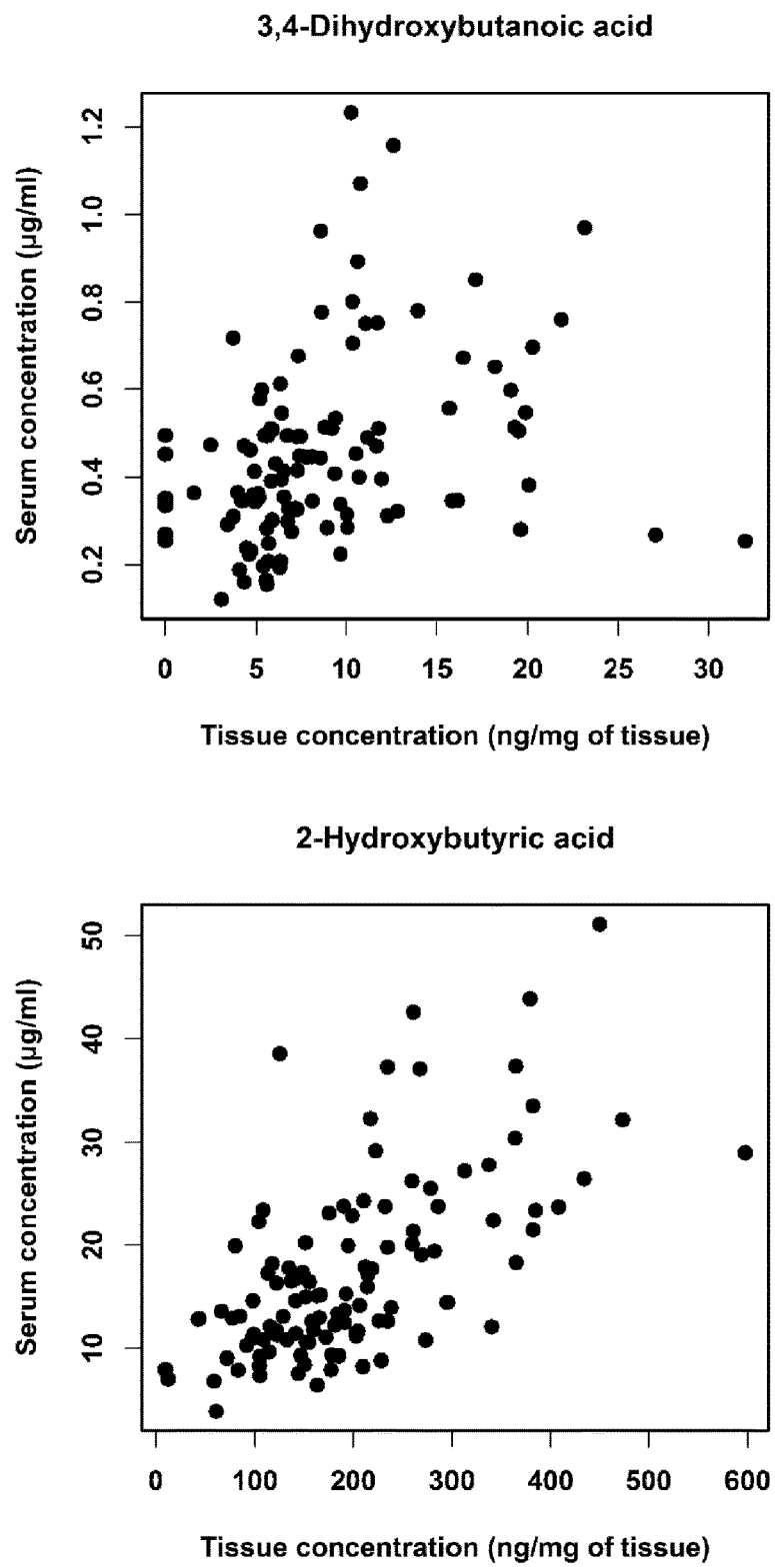
FIG. 6 discloses scatter plots visualizing the correlation between tissue and serum concentrations for selected small molecule biomarkers. The statistical results showing p- and R2-values in Spearman and Pearson correlation analyses are shown in Table 5.
Figure 6:
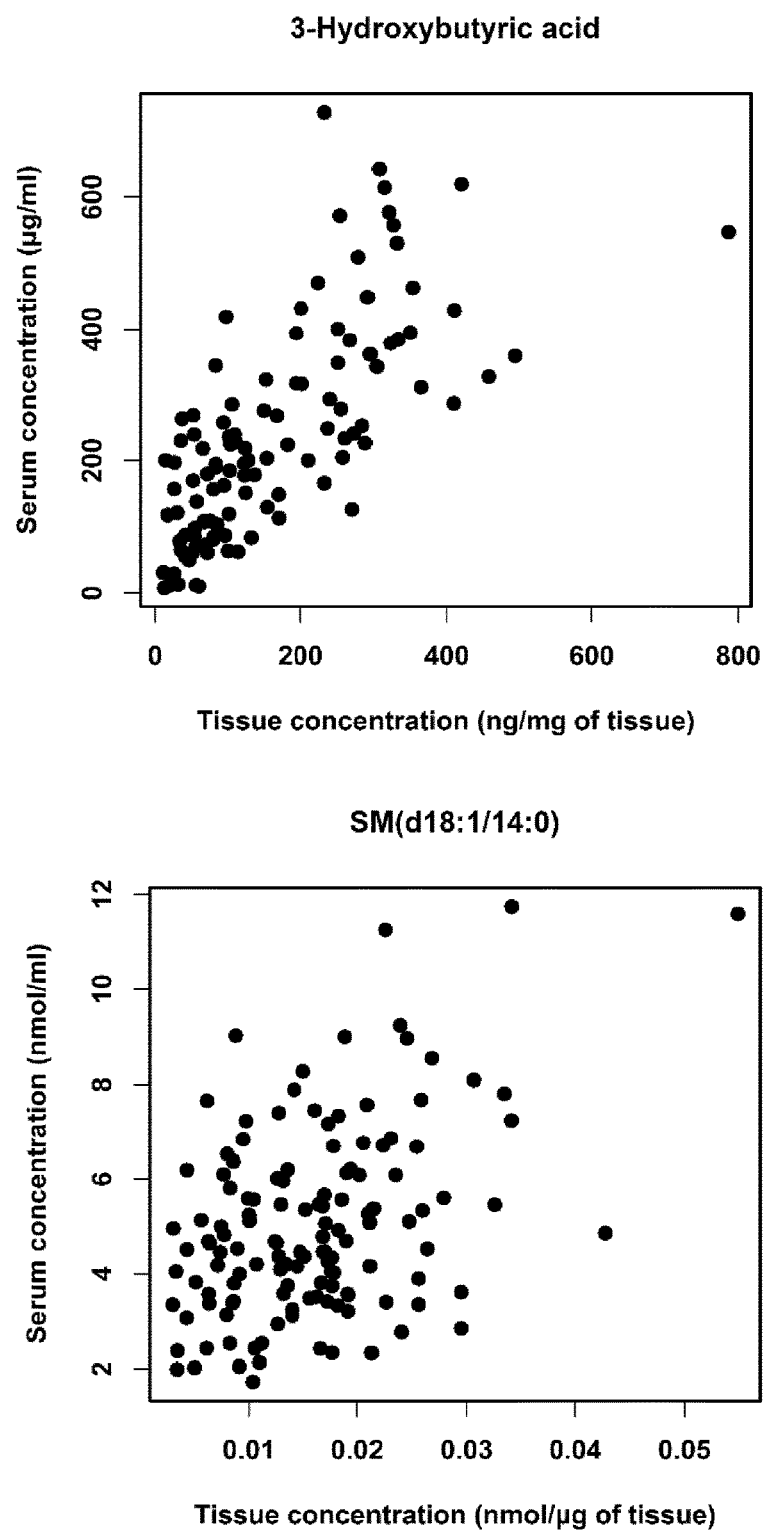
Figure 6:
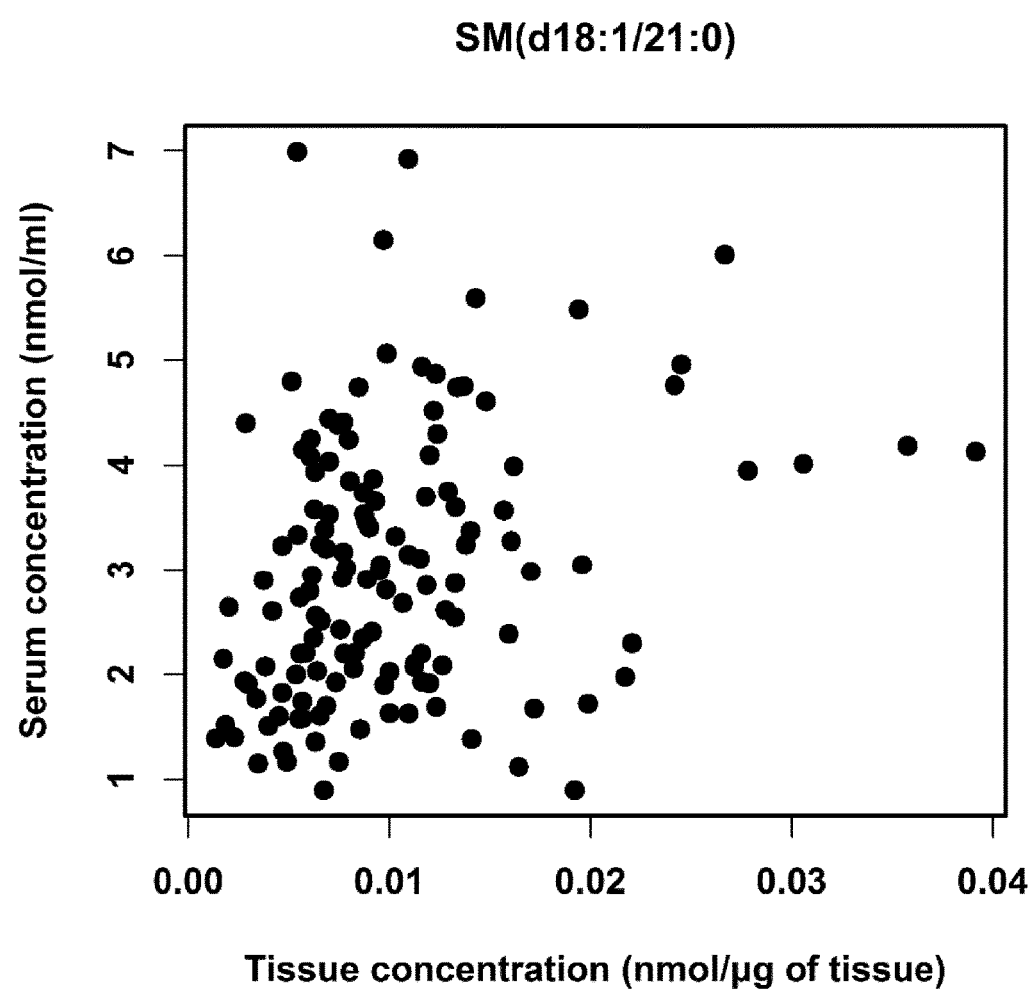

Small Molecule Biomarker Concentrations in the Serum Correlate with the Concentrations in the Tumor From the previous results it was evident that the presence of ovarian cancer causes changes of small biomarker concentrations in the serum of the patients. In order to investigate whether the same phenomenon can be observed also in the tumors of the same patients, the same methodologies were applied to tumor tissue samples, and the correlation of metabolites between the serum and tumor tissue was estimated with Pearson and Spearman correlation analyses. Table 5 shows the results for those small molecule biomarkers, which showed a statistically significant result (p<0.05) and R2 value >0.2 either in the Pearson or Spearman correlation analysis. As shown in Table 5, many of the small molecule biomarkers mentioned in the previous section showed significant correlation. The highest correlations were observed for hydroxybutyric acids, 3,4-dihydroxybutyric acid and sphingomyelins, and the results are illustrated in FIG. 6.

TABLE 5

Pearson and Spearman p- and R2-values for small molecule biomarkers, when the correlation between concentration in the serum and tissue sample is measured.

| Small molecule | Pearson | | Spearman | |
|---|---|---|---|---|
| | p-value | R2 | p-value | R2 |
| 3-Hydroxybutyric acid | <5.73E−14 | 0.722 | <5.73E−14 | 0.766 |
| 2-Hydroxybutyric acid | 5.73E−14 | 0.635 | <5.73E−14 | 0.602 |
| 3,4-Dihydroxybutyric acid | 4.69E−04 | 0.325 | 5.87E−06 | 0.413 |
| SM(d18:1/21:0) | 5.96E−04 | 0.293 | 2.41E−04 | 0.314 |
| SM(d18:1/14:0) | 6.59E−07 | 0.414 | 3.96E−04 | 0.303 |
| Adipic acid | 2.46E−02 | 0.212 | 2.48E−02 | 0.212 |
| 4-Hydroxyphenyllactic acid | 3.96E−03 | 0.270 | 2.63E−02 | 0.210 |
| 2,4-Dihydroxybutyric acid | 3.82E−02 | 0.196 | 4.04E−02 | 0.194 |
| 3-Hydroxyisovaleric acid | 3.24E−02 | 0.202 | 1.63E−01 | 0.133 |
| 2,3-Dihydroxybutyric acid | 9.23E−03 | 0.245 | 1.65E−01 | 0.132 |

Biological Significance of the Results

An interesting phenomenon observed in the results presented in previous sections is that the most promising small biomarkers for ovarian cancer diagnosis and prognosis are belonging only to a few compound classes. Oxidation of fatty acids produces ketone bodies, 3-hydroxybutyrate, acetoacetate and acetone. Of these three ketone bodies 3-hydroxybutyrate and acetoacetate were included in the data sets, and both of those were increased in the serum of ovarian cancer patients. In addition, compounds showing similar structure, i.e. 2-hydroxybutyric acid, 3,4-dihydroxybutyric acid, 2,3-dihydroxybutyric acid, 2,3,4-trihydroxybutyric acid and 3-hydroxyisovaleric acid (also known as beta-hydroxy beta-methylbutyric acid) were all increased in the serum of ovarian cancer patients, and most of these also showed strong prognostic value. Moreover, 3-hydroxybutyric and 2-hydroxybutyric acids showed strong correlations in their levels between serum and tumor. Finally, adipic acid, which also showed diagnostic and prognostic value, can be produced in human physiology by omega oxidation, which is another route of fatty acid oxidation. Thus, it is plausible that increased oxidation of fatty acids and increased production of ketone bodies are the key features of ovarian cancer metabolism that can explain the present results. Possible increased uptake of serum lipids may alter the serum and its lipoprotein composition, and therefore the decreased levels of sphingomyelins and their association with the prognosis of the patients are also likely explained by the altered lipid metabolism of ovarian cancer cells. The only small biomarker in the present study not showing a clear association with hydroxybutyric acid or lipid metabolism is 4-hydroxyphenyllactic acid, which may point in to the direction of amino acid catabolism in tumors.

Figure 7:
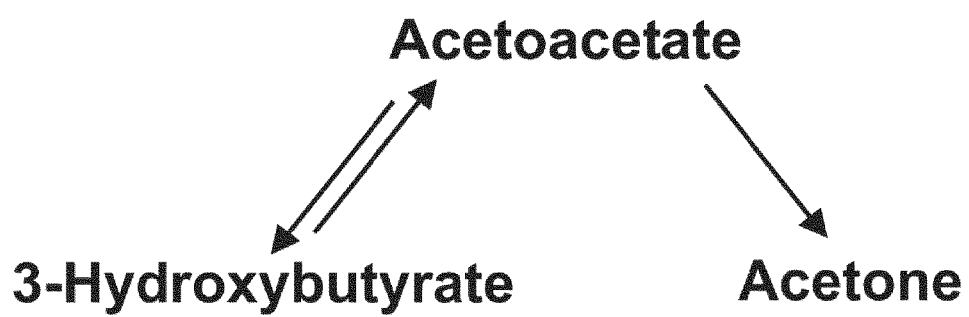
FIG. 7 discloses a simple schematic drawing illustrating the chemical reactions of ketone bodies in human body. 3-hydroxybutyrate can be converted in a reversible reaction into acetoacetate, which can be converted in an irreversible reaction into acetone. The results of the present study showed higher concentration of 3-hydroxybutyric acid and acetoacetic acid in the serum of ovarian cancer patients. According to these reactions it is logical that also the concentration of acetone is increased.

It is important to recognize that both beta-hydroxybutyric acid and acetoacetate were increased in ovarian cancer patients, and as shown in FIG. 7, beta-hydroxybutyrate can be converted to acetoacetate, which can be converted to acetone. Acetone is a volatile molecule, which can be detected in breath. Therefore, based on the present findings it is logical that acetone could be used as a diagnostic biomarker for ovarian cancer from the serum or breath of ovarian cancer patients.

The invention claimed is:

1. An in vitro screening method for assessing whether a subject is at risk to develop or is suffering from ovarian cancer, comprising:
   assaying a sample from said subject to determine a concentration of at least one small molecule biomarker, wherein an increase or decrease in the concentration of the at least one small molecule biomarker in said sample, when compared to a control sample, is indicative of said subject suffering from or having an increased risk of developing ovarian cancer; (1) wherein the at least one small molecule biomarker whose increase in concentration is compared to the control is a dihydroxybutyric acid and/or a trihydroxybutyric acid.

2. The method of claim 1, further comprising assaying said sample to determine a concentration of at least one additional small molecule biomarker wherein an increase in concentration of said at least one additional biomarker, when compared to a control sample, is indicative of said subject suffering from or having an increased risk of developing ovarian cancer;
   (a) wherein the at least one additional small molecule biomarker whose increase in concentration is compared to the control is a hydroxyacid and/or an adipic acid; and/or
   (b) wherein the at least one additional small molecule biomarker whose increase in concentration is compared to the control is a hydroxybutyric acid and/or ketone bodies.

3. The method of claim 2, wherein the assaying step comprises determining the concentration of:
   the dihydroxybutyric acid or the trihydroxybutyric acid;
   the hydroxyacid or the adipic acid; and/or
   the hydroxybutyric acid or ketone bodies.

4. The method of claim 1, further comprising measuring a level of one or more of CA-125 and/or HE4 in the sample from the subject, wherein an increased level of one or more of CA-125 and/or HE4 is indicative of the subject having an increased risk of developing or suffering from ovarian cancer when the screening method of claim 1 shows increased risk of developing or suffering from ovarian cancer.

5. A method of assessing whether a subject has a decreased survival prognosis for ovarian cancer, comprising:
   measuring the level of at least one small molecule biomarker in a sample from the subject, wherein an increase in the level of the at least one small molecule biomarker, relative to the level of the corresponding small molecule biomarker in a control sample, is indicative that the subject has a poor survival prognosis for the ovarian cancer, and wherein the at least one small molecule biomarker is a dihydroxybutyric acid or a trihydroxybutyric acid.

6. An in vitro method for assessing success rate of an ovarian cancer tumor removal in a subject, comprising measuring a concentration of at least one small molecule biomarker in a sample from the subject, wherein an increase or a decrease in the concentration of the at least one small molecule biomarker, relative to the concentration of the corresponding small molecule biomarker in a control sample, is indicative that the tumor removal was successful, and
(1) wherein the at least one small molecule biomarker whose decrease in concentration is compared to the control is a dihydroxybutyric acid and/or a trihydroxybutyric acid.

7. The method of claim 6, further comprising measuring a concentration of at least one additional small molecule biomarker from said sample, wherein a decrease in the concentration of said at least one additional small molecule biomarker, when compared to a control sample, is indicative that the tumor removal was successful;
(a) wherein the at least one additional small molecule biomarker whose decrease in concentration is compared to the control is a hydroxyacid and/or an adipic acid; and/or
(b) wherein the at least one additional small molecule biomarker whose decrease in concentration is compared to the control is a hydroxybutyric acid and/or ketone bodies.

8. The method of claim 7, wherein the measuring step comprises determining the level of:
the dihydroxybutyric acid or the trihydroxybutyric acid; and
the hydroxyacid or the adipic acid; and/or
hydroxybutyric acid or ketone bodies.

9. An in vitro method of evaluating effectiveness of an ovarian cancer therapy in a subject, comprising:
assaying a sample from said subject to determine a concentration of at least one first small molecule biomarker and/or a concentration of at least one second small molecule biomarker, wherein an increase or a decrease in concentration of the at least one first small molecule biomarker and/or second small molecule biomarker biomolecule in said sample, when compared to a control sample, is indicative of effectiveness of said ovarian cancer therapy;
(1) wherein the at least one first small molecule biomarker whose concentration is compared to the control is a dihydroxybutyric and/or a trihydroxybutyric acid; and
(a) wherein the at least one second small molecule biomarker whose concentration is compared to the control is a dihydroxyacid and/or an adipic acid; and/or
(b) wherein the at least one second small molecule biomarker whose concentration is compared to the control is a hydroxybutyric acid and/or ketone bodies;
and wherein said increase in at least one of (1), (a), and (b) is indicative of ineffective treatment; and/or
decrease in at least one of (1), (a), and (b) is indicative of effective treatment.

10. The method of claim 9, wherein the ovarian cancer therapy comprises administering a pharmaceutical agent affecting lipid metabolism.

11. An in vitro method of determining concentration of a metabolite in ovarian tissue of a subject, comprising:
assaying a blood sample obtained from the subject to determine a concentration of the metabolite; comparing the concentration of the metabolite with a concentration in a control sample wherein an increase in a level of the metabolite compared to the control sample is indicative that the subject has increased concentration of the metabolite in ovarian tissue; and wherein the metabolite is 3,4-dihydroxybutyric acid, 2,4-dihydroxybutyric acid, and/or 2,3-dihydroxybutyric acid.

12. The method of claim 1, wherein the method comprises determining the concentration of 2, 3, 4, 5, 6, 7, 8, 9, 10 or more small molecule biomarkers.

13. The method of claim 1, wherein the biomarker concentration is determined by using mass spectrometry, nuclear magnetic resonance spectroscopy, fluorescence spectroscopy or dual polarisation interferometry, an immunoassay, enzymatic assay, colorimetric assay, fluorometric assay, a rapid test, a breath test and/or with a binding moiety capable of specifically binding the biomarker.

14. The method of claim 1, wherein the at least one small molecule biomarker whose increase in concentration is compared to the control is the dihydroxybutyric acid and/or trihydroxybutyric acid, and the dihydroxybutyric acid is 2,4-dihydroxybutyric acid, 3,4-dihydroxybutyric acid, and/or 2,3-dihydroxybutyric acid, and/or the trihydroxybutyric acid is 2,3,4-trihydroxybutyric acid.

15. The method of claim 1, wherein the ovarian cancer is early stage ovarian cancer.

16. The method of claim 9, further comprising a step of administering the ovarian cancer therapy to the subject, wherein the ovarian cancer therapy was determined to be effective for treating cancer in the method of claim 9.

17. The method of claim 2, wherein the at least one additional small molecule biomarker whose increase in concentration is compared to the control is the hydroxyacid or ketone bodies, wherein the hydroxyacid is 4-hydroxyphenyllactic acid and/or 3-hydroxyisovaleric acid, and wherein the ketone bodies are acetone or acetoacetic acid.

18. The method of claim 2, wherein the at least one additional small molecule biomarker whose increase in concentration is compared to the control is the hydroxybutyric acid, wherein the hydroxybutyric acid is 3-hydroxybutyric acid and/or 2-hydroxybutyric acid.

19. The method of claim 2, further comprising measuring a level of one or more of CA-125 and/or HE4 in the sample from the subject, wherein an increased level of one or more of CA-125 and/or HE4 is indicative of the subject having an increased risk of developing or suffering from ovarian cancer when the method of claim 2 shows increased risk of developing or suffering from ovarian cancer.

20. The method of claim 5, wherein the method comprises determining the concentration of 2, 3, 4, 5, 6, 7, 8, 9, 10 or more small molecule biomarkers.

21. The method of claim 6, wherein the method comprises determining the concentration of 2, 3, 4, 5, 6, 7, 8, 9, 10 or more small molecule biomarkers.

22. The method of claim 9, wherein the method comprises determining the concentration of 2, 3, 4, 5, 6, 7, 8, 9, 10 or more small molecule biomarkers.

23. The method of claim 5, wherein the biomarker concentration is determined by using mass spectrometry, nuclear magnetic resonance spectroscopy, fluorescence spectroscopy or dual polarisation interferometry, an immunoassay, enzymatic assay, colorimetric assay, fluorometric assay, a rapid test, a breath test and/or with a binding moiety capable of specifically binding the biomarker.

24. The method of claim 6, wherein the biomarker concentration is determined by using mass spectrometry, nuclear magnetic resonance spectroscopy, fluorescence spectroscopy or dual polarisation interferometry, an immunoassay, enzymatic assay, colorimetric assay, fluorometric assay, a rapid test, a breath test and/or with a binding moiety capable of specifically binding the biomarker.

25. The method of claim 9, wherein the biomarker concentration is determined by using mass spectrometry, nuclear magnetic resonance spectroscopy, fluorescence spectroscopy or dual polarisation interferometry, an immunoassay, enzymatic assay, colorimetric assay, fluorometric assay, a rapid test, a breath test and/or with a binding moiety capable of specifically binding the biomarker.

26. The method of claim 5, wherein the at least one small molecule biomarker whose increase in concentration is compared to the control is the dihydroxybutyric acid and/or trihydroxybutyric acid, wherein the dihydroxybutyric acid is 2,4-dihydroxybutyric acid, 3,4-dihydroxybutyric acid, and/or 2,3-dihydroxybutyric acid, and/or wherein the trihydroxybutyric acid is 2,3,4-trihydroxybutyric acid.

27. The method of claim 6, wherein the at least one small molecule biomarker whose decrease in concentration is compared to the control is the dihydroxybutyric acid and/or trihydroxybutyric acid, wherein the dihydroxybutyric acid is 2,4-dihydroxybutyric acid, 3,4-dihydroxybutyric acid, and/or 2,3-dihydroxybutyric acid, and/or wherein the trihydroxybutyric acid is 2,3,4-trihydroxybutyric acid.

28. The method of claim 9, wherein the at least one first small molecule biomarker whose concentration is compared to the control is the dihydroxybutyric acid and/or trihydroxybutyric acid, wherein the dihydroxybutyric acid is 2,4-dihydroxybutyric acid, 3,4-dihydroxybutyric acid, and/or 2,3-dihydroxybutyric acid, and/or wherein the trihydroxybutyric acid is 2,3,4-trihydroxybutyric acid.

29. The method of claim 1, further comprising a step of administering ovarian cancer therapy to the subject, wherein the subject was determined to be at risk to develop or suffering from ovarian cancer according to the method of claim 1.

30. The method of claim 5, further comprising a step of administering ovarian cancer therapy to the subject, wherein the subject was determined to have a decreased survival prognosis for ovarian cancer according to the method of claim 5.

31. The method of claim 6, further comprising a step of administering ovarian cancer therapy to the subject, wherein the tumor removal was determined to be unsuccessful according to the method of claim 6.

32. The method of claim 1, further comprising assaying said sample to determine a concentration of at least one additional small molecule biomarker, wherein an increase or decrease in concentration of said at least one additional biomarker, when compared to a control sample, is indicative of said subject suffering from or having an increased risk of developing ovarian cancer;
    (a) wherein the at least one additional small molecule biomarker whose decrease in concentration is compared to the control is a sphingomyelin;
    (b) wherein the at least one additional small molecule biomarker whose increase in concentration is compared to the control is a long chain triglyceride having acyl side chains comprising at least 54 carbon atoms in total; and/or
    (c) wherein the at least one additional small molecule biomarker whose decrease in concentration is compared to the control is a triglyceride having acyl side chains comprising less than 54 carbon atoms in total.

33. The method of claim 5, further comprising assaying said sample to determine a concentration of at least one additional small molecule biomarker, wherein an increase or decrease in the concentration of said at least one additional biomarker, when compared to a control sample, is indicative of said subject having a poor survival prognosis for ovarian cancer, and
    (a) wherein the at least one additional small molecule biomarker whose increase in concentration is compared to the control is a hydroxyacid, an adipic acid, a hydroxybutyric acid, and/or ketone bodies;
    (b) wherein the at least one additional small molecule biomarker whose decrease in concentration is compared to the control is a sphingomyelin.

34. The method of claim 6, further comprising assaying said sample to determine a concentration of at least one additional small molecule biomarker, wherein an increase or decrease in the concentration of said at least one additional biomarker, when compared to a control sample, is indicative that the tumor removal was successful;
    (a) wherein the at least one additional small molecule biomarker whose increase in concentration is compared to the control is a sphingomyelin;
    (b) wherein the at least one additional small molecule biomarker whose decrease in concentration is compared to the control is a long chain triglyceride having acyl side chains comprising at least 54 carbon atoms in total; and/or
    (c) wherein the at least one additional small molecule biomarker whose increase in concentration is compared to the control is a triglyceride having acyl side chains comprising less than 54 carbon atoms in total.

35. The method of claim 9, further comprising assaying said sample to determine a concentration of at least one additional small molecule biomarker, wherein an increase or decrease in the concentration of said at least one additional biomarker, when compared to a control sample, is indicative of effectiveness of said ovarian cancer therapy;
    (a) wherein the at least one additional small molecule biomarker whose concentration is compared to the control is a sphingomyelin;
    (b) wherein the at least one additional small molecule biomarker whose concentration is compared to the control is a long chain triglyceride having acyl side chains comprising at least 54 carbon atoms in total; and/or
    (c) wherein the at least one additional small molecule biomarker whose concentration is compared to the control is a triglyceride having acyl side chains comprising less than 54 carbon atoms in total;
and wherein said decrease in at least one of (a) and (c), or said increase in (b) is indicative of ineffective treatment; and/or said increase in at least one of (a) and (c), or said decrease in (b) is indicative of effective treatment.

36. The method of claim 11, further comprising assaying said sample to determine a concentration of at least one additional metabolite, wherein the at least one additional metabolite is 3-hydroxybutyric acid, 2-hydroxybutyric acid, SM(d18:1/21:0), SM(d18:1/14:0), adipic acid, 4-hydroxyphenyllactic acid and/or 3-hydroxyisovaleric acid.

* * * * *

UNITED STATES PATENT AND TRADEMARK OFFICE
CERTIFICATE OF CORRECTION

PATENT NO. : 10,534,001 B2
APPLICATION NO. : 15/513755
DATED : January 14, 2020
INVENTOR(S) : Mika Hilvo Page 1 of 1

It is certified that error appears in the above-identified patent and that said Letters Patent is hereby corrected as shown below:

In the Claims

In Claim 1, Column 24, Line 26, "or decrease" should be deleted,

In Claim 6, Column 25, Lines 11-12, "an increase or" should be deleted,

In Claim 9, Column 25, Line 46, "an increase or" should be deleted, and

In Claim 9, Column 25, Line 49, "biomolecule" should be deleted.

Signed and Sealed this
Twenty-fifth Day of February, 2020

Andrei Iancu
*Director of the United States Patent and Trademark Office*